United States Patent [19]

Watanabe et al.

[11] Patent Number: 5,753,619
[45] Date of Patent: May 19, 1998

[54] COMPOSITION FOR PROPHYLAXIS OR TREATMENT OF PULMONARY CIRCULATORY DISEASES

[75] Inventors: Toshifumi Watanabe; Keiji Kusumoto; Mitsuhiro Wakimasu, all of Osaka, Japan

[73] Assignee: Takeda Chemical Insustries, Ltd., Osaka, Japan

[21] Appl. No.: 564,442

[22] Filed: Nov. 29, 1995

[30] Foreign Application Priority Data

Dec. 1, 1994 [JP] Japan ................... 6-298193

[51] Int. Cl.$^6$ ................ C07K 7/64; A61K 37/02
[52] U.S. Cl. ................ 514/11; 514/17; 530/317; 530/329
[58] Field of Search ................ 514/11; 530/317

[56] References Cited

FOREIGN PATENT DOCUMENTS

| | | |
|---|---|---|
| 0 528 312 A2 | 2/1993 | European Pat. Off. . |
| 0 552 417 A1 | 7/1993 | European Pat. Off. . |
| 0 655 463 A1 | 5/1995 | European Pat. Off. . |
| WO 93/25580 | 12/1993 | WIPO . |

OTHER PUBLICATIONS

S.T. Bonvallet et al., American Journal of Physiology, vol. 266, H1327–H1331 (1994).

T. Miyauchi, et al., Circulation Research, "Contribution of Endogenous Endothelin–1 to the Progression of Cardiopulmonary Alterations in Rats With Monocrotaline–Induced Pulmonary Hypertension", vol. 73, No. 5, 887–897 (1993).

*Primary Examiner*—Cecilia J. Tsang
*Assistant Examiner*—Michael L. Borin
*Attorney, Agent, or Firm*—David G. Conlin; Cara Z. Lowen

[57] ABSTRACT

Cyclic hexapeptides having antagonistic activity on endothelin receptors of the formula [I]:

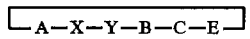

wherein X and Y each is an α-amino acid residue having D-, L-form or DL-form, A is a D-acidic-α-amino acid residue, B is a neutral-α-amino acid residue having D- or L-form, C is an L-α-amino acid residue and E is a D-α-amino acid residue having an aromatic ring group can be effectively used for prophylaxis and/or treatment of pulmonary circulatory diseases.

15 Claims, No Drawings

COMPOSITION FOR PROPHYLAXIS OR TREATMENT OF PULMONARY CIRCULATORY DISEASES

The present invention relates to a pharmaceutical composition for the prophylaxis or treatment of pulmonary circulatory diseases, the composition comprising an effective amount of compounds having antagonistic activity on endothelin receptors.

PRIOR ART

Endothelin (ET) was discovered and identified as a peptide composed of 21 amino acid residues [M. Yanagisawa et al., *Nature* 332, 411–412 (1988)]. As to endothelin, various physiological activities such as cardiac stimulating activity and renal mesangial contractive activity, including vasoconstrictive activity have been reported. Further, for endothelin, the presence of at least three kinds of isoforms (ET-1, ET-2 and ET-3) and two receptors ($ET_A$ and $ET_B$) has been reported.

Since the discovery of endothelin, the present inventors have searched compounds having antagonistic activity on endothelin receptors, and have discovered the group of compounds described in Japanese Unexamined Patent Publication No. 6-9689 (EP 0528312A2), which discloses that these compounds are effective as therapeutic drugs for treating hypertension, cardiac or cerebral circulatory diseases, renal diseases and asthma are useful, anti-inflammatory drugs, antarthritics and the like. Further, these compounds can also be used for the prophylactic and/or therapeutic treatment of hypofunction of organs and complications in their surgery or transplant or thereafter.

On the other hand, patients suffering from pulmonary hypertension, a pulmonary circulatory disease distinguished from systemic hypertension, are known to have an increased endothelin concentration in their serum, and the correlation between the increased endothelin concentration and pulmonary arterial pressure has been shown. Further, cyclic pentapeptides and straight chain tripeptides having antagonistic activity on endothelin receptor $ET_A$ have been reported to induce a reduction in pulmonary arterial pressure in a pulmonary hypertension model [*Circulation Research* 73, No. 5, 887–897 (1993) and *American Journal of Physiology* H1327-H1331 (1994)]. However, peptide compounds different from the cyclic pentapeptides and the straight chain tripeptides in structure, the peptide compounds having antagonistic activity on endothelin receptors, and the effect thereof on this disease have not been described nor suggested.

Furthermore, no compounds having pharmacological action other than antagonistic activity on endothelin receptors have been shown to have clinical effectiveness and usefulness as prophylactic and/or therapeutic compositions for the treatment of pulmonary circulatory diseases.

Under such circumstances, preparations clinically useful for the prophylactic and/or therapeutic treatment of pulmonary circulatory diseases different from systemic hypertension or cardiac or cerebral circulatory diseases were developed.

SUMMARY OF THE INVENTION

The present inventors have found that cyclic hexapeptides different from cyclic pentapeptides and the straight chain tripeptides in structure, the cyclic pentapeptides having antagonistic activity on endothelin receptors $ET_A$ and $ET_B$, are unexpectedly effective for the prophylaxis and treatment of pulmonary circulatory diseases.

According to the present invention, there is provided a pharmaceutical composition for the prophylaxis or treatment of pulmonary circulatory diseases which comprises a cyclic hexapeptide of the formula [I]:

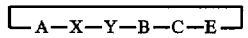

[I]

wherein X and Y each is an a-amino acid residue having D-, L-form or DL-form, A is a D-acidic-α-amino acid residue, B is a neutral-α-amino acid residue having D- or L-form, C is an L-α-amino acid residue and E is a D-α-amino acid residue having an aromatic ring group; or a pharmaceutically acceptable ester or salt thereof, if necessary, with a pharmaceutically acceptable excipient, carrier or diluent.

In formula [I], an amino acid which forms the α-amino acid residue represented by X or Y may be any amino acid as long as it is an α-amino acid. Examples thereof include alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, proline, 4-hydroxyproline, thioproline, azetidine-2-carboxylic acid, pipecolic acid (piperidine-2-carboxylic acid), indoline-2-carboxylic acid, tetrahydroisoquinoline-3-carboxylic acid, serine, threonine, tryptophan, 5-methyltryptophan, tyrosine, valine, alloisoleucine, norvaline, norleucine, tertiary leucine, γ-methylleucine, phenylglycine, 2-aminobutyric acid, cysteic acid, homocysteic acid, 1-naphthylalanine, 2-naphthylalanine, 2-thienylglycine, 3-thienylglycine, 3-benzothienyl-alanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid. When these α-amino acids have functional groups such as hydroxyl, thiol, amino, imino and carboxyl, these functional groups may be substituted.

The substituted hydroxyl groups include $C_{1-6}$ alkanoyloxy (for example, formyloxy, acetyloxy and propionyloxy), $C_{4-9}$ alicyclic carbonyloxy (for example, cyclopentanecarbonyloxy and cyclohexanecarbonyloxy), $C_{7-15}$ arylcarbonyloxy (for example, benzoyloxy and 4-methylbenzoyloxy), $C_{8-16}$ aralkylcarbonyloxy (for example, phenylacetoxy, 2-phenylpropionyloxy, 3-phenylpropionyloxy and diphenylacetoxy) and aromatic heterocyclicalkylcarbonyloxy (for example, indole-2-ylacetoxy and indole-3-ylacetoxy); and $C_{1-6}$ alkoxy (for example, methoxy, ethoxy, n-propoxy and t-butoxy), $C_{3-8}$ cycloalkyloxy (for example, cyclopentyloxy and cyclohexylxoy), $C_{6-12}$ aryloxy (for example, phenyloxy and 4-methylphenyloxy) and $C_{7-15}$ aralkyloxy (for example, benzyloxy, phenethyloxy and diphenylmethyloxy). Examples of the α-amino acids whose hydroxyl groups are substituted include 0-acetylserine, 0-acetylthreonine, 4-acetoxyproline, 0-benzoylserine, 0-benzoylthreonine, 4-benzoyloxyproline, 0phenylacetylserine, 0-phenylacetylthreonine, 4-phenylacetoxyproline, 0-ethylserine, 0-ethylthreonine, 4-ethoxyproline, 0-cyclohexylserine, 0-cyclohexylthreonine, 4-cyclohexyloxyproline, 0-phenylserine, 0-phenylthreonine, 4-phenoxyproline, 0-benzylserine, 0-benzylthreonine, 4-benzyloxyproline, 0-diphenylmethylserine, 0-diphenylmethylthreonine and 4-diphenylmethoxyproline.

The substituted thiol groups include thiol esters such as $C_{1-6}$ alkanoylthio (for example, formylthio, acetylthio and propionylthio), C$_{4-9}$ alicyclic carbonylthio (for example, cyclopentanecarbonylthio and cyclohexanecarbonylthio), C$_{7-15}$ arylcarbonylthio (for example, benzoylthio and 4-methylbenzoylthio) and C$_{8-16}$ aralkylcarbonylthio (for example, phenylacetylthio, 2-phenylpropionylthio, 3-phenylpropionylthio and diphenylacetylthio); and C$_{1-6}$ alkylthio (for example, methylthio, ethylthio, n-propylthio and t-butylthio), C$_{3-8}$ cycloalkylthio (for example, cyclopentylthio and cyclohexylthio), C$_{6-12}$ arylthio (for example, phenylthio and 4-methylphenylthio) and C$_{7-15}$ aralkylthio (for example, benzylthio, phenethylthio and diphenylmethylthio). Examples of the α-amino acids whose thiol groups are substituted include S-acetyl-cysteine, S-benzoylcysteine, S-phenylacetylcysteine, S-ethylcysteine, S-cyclohexylcysteine, S-phenylcysteine and S-benzyl-cysteine.

The substituted amino groups include C$_{1-6}$ alkylamino [for example, N-methylamino, N-ethylamino and N-t-butylamino], C$_{3-8}$ cycloalkyl-amino [for example, N-cyclopentylamino and N-cyclohexylamino], C$_{6-12}$ arylamino [for example, N-phenylamino and N-{4-methylphenyl}amino], C$_{7-15}$ aralkylamino [for example, N-benzylamino, N-phenethylamino, N-{2-chlorobenzyl}amino, N-{3-chlorobenzyl}amino, N-{4-chlorobenzyl}amino, N-{2-methylbenzyl}amino, N-{3methyl-benzyl}amino, N-{4-methylbenzyl}amino, N-{2-methoxybenzyl}amino, N-{3-methoxy-benzyl}amino and N-{4-methoxybenzyl}amino] and aromatic heterocyclic-C$_{1-6}$ alkylamino [for example, 2-furylmethylamino, 3-furylmethylamino, 2-thienylmethylamino, 3-thienylmethylamino, indole-2-ylmethylamino and indole-3-ylmethylamino]; and also include substituted amido groups such as C$_{1-6}$ aliphatic acylamido [for example, formamido, acetamido and propionamido], C$_{4-9}$ alicyclic acylamido [for example, cyclopentanecarbonylamido and cyclohexanecarbonylamido], C$_{7-15}$ arylacylamido [for example, benzamido and 4-methylbenzamido], C$_{8-16}$ aralkylacylamido [for example, phenylacetamido, 2-phenylpropionamido, 3-phenylpropionamido, diphenylacetamido, 1-naphthylacetamido and 2-naphthyl-acetamido], aromatic heterocycliccarbonylamido [for example, indole-2-ylcarbonylamido and indole-3-ylcarbonylamido], aromatic heterocyclic-alkylcarbonylamido [for example, indole-2-ylacetamido and indole-3-ylacetamido], and sulfonylamido [for example, benzenesulfonylamido, p-toluenesulfonylamido and 4-methoxy-2,3,6-trimethylbenzenesulfonylamido]. The substituents in the substituted imino group include C$_{1-6}$ alkyl, C$_{3-8}$ cycloalkyl, C$_{6-12}$ aryl, C$_{7-15}$ aralkyl and aromatic heterocyclic C$_{1-6}$ alkyl groups which are the same ones in the substituted amino groups. Examples of the α-amino acids whose amino groups are substituted include N-methylglycine (sarcosine), N-ethylglycine, N-methylleucine, N-ethyl-leucine, N-methylphenylalanine, N-ethylphenylalanine, N(α)-methyltryptophan, N(α)-ethyltryptophan, N-cyclopentylglycine, N-cyclohexylglycine, N-phenylglycine, N-phenylleucine, N-benzylglycine, N-benzylleucine, N(π)-benzylhistidine, N(τ)-benzylhistidine, N(π)-phenacylhistidine, N(π)-benzyloxymethylhistidine, N$^g$-benzenesulfonylarginine, N$^g$-p-toluenesulfonylarginine, N$^g$-(4-methoxy-2,3,6-trimethylbenzenesulfonyl)arginine, N(ε)-benzenesulfonyllysine, N(ε)-p-toluenesulfonyllysine, N(ε)-(4-methoxy-2,3,6-trimethylbenzenesulfonyl))lysine, N$^{in}$-methyltryptophan, N$^{in}$-ethyltryptophan, N$^{in}$-formyltryptophan, N$^{in}$-acetyltryptophan, N(ε)-benzyllysine, N(ε)-(2-furylmethyl)lysine, N(ε)-(2-thienylmethyl)lysine, N(ε)-(indole-3-ylmethyl)lysine, N(ε)-phenylacetyllysine, N(ε)-({2-furyl}acetyl)lysine, N(ε)-({2-thienyl}acetyl)lysine, N(ε)-({indole-3-yl}acetyl)lysine, N(ε)-benzoyllysine, N(ε)-(3-phenylpropionyl)lysine, N(δ)-benzylornithine, N(δ)-(2-furylmethyl)ornithine, N(δ)-(2-thienylmethyl)ornithine, N(δ)-(indole-3-ylmethyl)ornithine, N(δ)-benzoylornithine, N(δ)-phenylacetylornithine, N(δ)-(3-phenylpropionyl)-ornithine, N(δ)-({2-methylphenyl}acetyl)ornithine, N(δ)-({3-methylphenyl}acetyl)ornithine, N(δ)-({4-methylphenyl}acetyl)ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl)ornithine, N(γ)-benzyl-2,4-diaminobutyric acid, N(γ)-(2-furylmethyl)-2,4-diaminobutyric acid, N(γ)-(2-thienylmethyl)-2,4-diaminobutyric acid, N(γ)-(indole-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2-furylacetyl)-2,4-diaminobutyric acid, N(γ)-(2-thienylacetyl)-2,4-diaminobutyric acid and N(γ)-({inole-3-yl}acetyl)- 2,4-diaminobutyric acid.

The substituted carboxyl groups include amido groups such as a carbamoyl group (—CONH$_2$), C$_{1-6}$ alkylcarbamoyl (for example, methylcarbamoyl, ethylcarbamoyl, {n-propyl}-carbamoyl and t-butylcarbamoyl), C$_{3-8}$ cycloalkylcarbamoyl (for example, cyclopentylcarbamoyl and cyclohexylcarbamoyl), C$_{6-12}$ arylcarbamoyl (for example, phenylcarbamoyl and {4-methylphenyl}carbamoyl), C$_{7-15}$ aralkylcarbamoyl (for example, benzylcarbamoyl, phenethylcarbamoyl, {1,2-diphenylethyl}carbamoyl), {aromatic heterocyclic-C$_{1-6}$ alkyl}carbamoyl (for example, [2-{indole-2-yl}ethyl] carbamoyl and [2-{indole-3-yl}ethyl]carbamoyl), piperidinocarbonyl, piperazinecarbonyl, N$^4$-C$_{1-6}$ alkyl-piperazinecarbonyl (for example, N$^4$-methylpiperazinecarbonyl and N$^4$-ethylpiperazinecarbonyl), N$^4$-C$_{3-8}$ cycloalkylpiperazinecarbonyl (for example, N$^4$-cyclopentylpiperazinecarbonyl and N$^4$-cyclohexylpiperazinecarbonyl), N$^4$-(5 to 7 membered heterocyclicpiperazinecarbonyl (for example N$^4$-pyridylpiperazinecarbonyl, N$^4$-furylpiperazinecarbonyl, N$^4$-thienylpiperazinecarbonyl), N$^4$-C$_{6-12}$ arylpiperazinecarbonyl (for example, N$^4$-phenylpiperazinecarbonyl and N$^4$-{4-methylphenyl}-piperazinecarbonyl), N$^4$-C7-15 aralkylpiperazinecarbonyl (for example, N$^4$-benzylpiperazinecarbonyl, N$^4$-phenetylpiperazinecarbonyl, N$^4$-{1,2-diphenylethyl}-piperazinecarbonyl), N$^4$-{aromatic heterocyclic-C$_{1-6}$ alkyl}piperazinecarbonyl (for example, N$^4$-[2-{indole-2-yl}ethyl]piperazinecarbonyl and N$^4$-[2-{indole-3-yl}ethyl]piperazinecarbonyl), N$^4$-C$_{1-6}$ aliphatic acylpiperazine-carbonyl (for example, N$^4$-acetylpiperazinecarbonyl and N$^4$-propionylpiperazinecarbonyl), N$^4$-C49 alicyclic acylpiperazine-carbonyl (for example, N$^4$-cyclopentanecarbonylpiperazinecarbonyl N$^4$-C$_{7-15}$ arylacylpiperazinecarbonyl (for example, N$^4$-benzoylpiperazine-carbonyl and N$^4$-{4-methylbenzoyl}piperazinecarbonyl), N$^4$-C$_{8-16}$ aralkylacylpiperazinecarbonyl (for example, N4-phenylacetyl-piperazinecarbonyl N$^4$-{2-phenylpropion}-piperazinecarbonyl, N$^4$-{3-phenylpropionyl}piperazinecarbonyl, N$^4$-diphenylacetyl-piperazinecarbonyl), N$^4$-{1- naphthylacetyl}piperazinecarbonyl and $N^4$-{2-naphthylacetyl}piperazinecarbonyl),$N^4$-{aromatic heterocycliccarbonyl}piperazinecarbonyl (for example, $N^4$-{indole-2-ylcarbonyl}piperazinecarbonyl and $N^4$-{indole-3-ylcarbonyl}piperazinecarbonyl), and $N^4$-{aromatic heterocyclic-alkylcarbonyl}piperazinecarbonyl (for example, $N^4$-{indole-2-ylacetyl}piperazinecarbonyl and $N^4$-{indole-3-ylacetyl}-piperazinecarbonyl); and $C_{1-6}$ alkoxycarbonyl (for example, methoxycarbonyl, ethoxycarbonyl and n-propoxycarbonyl), $C_{3-8}$ cycloalkoxycarbonyl (for example, cyclopentyloxycarbonyl and cyclohexyloxycarbonyl) and $C_{7-15}$ aralkyloxycarbonyl (for example, benzyloxycarbonyl, phenetyloxycarbonyl, 1-phenylethyloxycarbonyl and diphenylmethyloxycarbonyl). The above-mentioned amido forms also include amido groups with α-amino acids and amido groups with oligopeptides (for example, dipeptides, tripeptides and tetrapeptides). The α-amino acids whose carboxyl groups are substituted include, for example, $N^4$-methylasparagine, $N^4$-phenylasparagine, $N^4$-benzylasparagine, $N^4$-phenethylasparagine, $N^4$-(2-{indole-3-yl}ethyl) -asparagine, $N^5$-methylglutamine, $N^5$-phenyl-glutamine, N5-benzylglutamine, $N^5$-phenethylglutamine, $N^5$-(2-{indole-3-yl}ethyl) glutamine, aspartic acid β-methyl ester, aspartic acid β-cyclopropyl ester, aspartic acid 0-benzyl ester, aspartic acid β-phenethyl ester, aspartic acid β-$N^4$phenylpiperazineamide, aspartic acid β$N^4$-(2-methylphenyl)piperazineamide, aspartic acid β-$N^4$-(3-methylphenyl)piperazineamide, aspartic acid β-$N^4$-(4-methylphenyl)piperazineamide, aspartic acid β-$N^4$-(2-methoxyphenyl)piperazineamide, aspartic acid β-$N^4$-(3-methoxyphenyl)piperazineamide, aspartic acid β-$N^4$-(4-methoxyphenyl)piperazineamide, aspartic acid β-$N^4$-(2-chlorophenyl)piperazineamide, aspartic acid β-$N^4$-(3-chlorophenyl)piperazineamide, aspartic acid β-$N^4$-(4-chlorophenyl)piperazineamide, aspartic acid β-$N^4$-(4-nitrophenyl)piperazineamide, aspartic acid β-$N^4$-(4-fluorophenyl)piperazineamide, aspartic acid β-$N^4$-(3-trifluoromethylphenyl)piperazineamide, aspartic acid β-$N^4$-(2,3-dimethyphenyl)piperazineamide, aspartic acid β-$N^4$-(2-pyridyl)piperazineamide, aspartic acid β-$N^4$-(2-pyrimidyl)piperazineamide, glutamic acid γ-methyl ester, glutamic acid γ-cyclopropyl ester, glutamic acid γ-benzyl ester and glutamic acid γ-phenethyl ester.

The α-amino acid which forms the amino acid residue represented by X or Y in formula [I] may be any of the L-, D- and DL-forms. The L-form is, however, more preferred in each case.

X preferably represents the following formula:

wherein G represents the following partial structural formula:

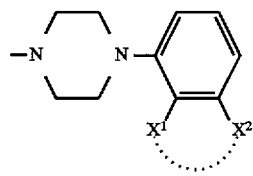

wherein $X^1$ and $X^2$ each is a hydrogen atom, a $C_1$ alkyl group, a $C_{1-6}$ alkoxy group, a halogen atom or a nitro group, and

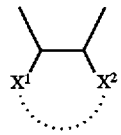

indicates that $X^1$ and $X^2$ may combine together to form a ring.

The $C_{1-6}$ alkyl groups represented by $X^1$ and $X^2$ include, for example, methyl, ethyl, n-propyl, iso-propyl, n-butyl, iso-butyl, tert-butyl, n-pentyl and n-hexyl. In particular, $C_{1-3}$ alkyl groups such as methyl, ethyl, n-propyl and iso-propyl are preferably used, and methyl is more preferred among others.

The $C_{1-6}$ alkoxy groups represented by xi and $X^2$ include, for example, methoxy, ethoxy, n-propoxy, n-butoxy, n-pentyloxy and n-hexyloxy. In particular, $C_{1-3}$ alkoxy groups such as methoxy, ethoxy and n-propoxy are preferably used, and methoxy and ethoxy are more preferred among others.

The halogen atoms represented by $X^1$ and $X^2$ include, for example, fluorine, chlorine, bromine and iodine. In particular, chlorine is preferably used.

When $X^1$ and $X^2$ combine together to form a ring, G is preferably a group represented by the following formula:

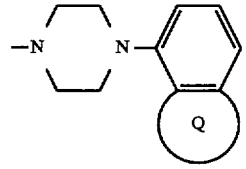

wherein examples of rings Q include 4- to 7-membered rings (such as a saturated carbon ring, an aromatic carbon ring, a saturated heterocyclic ring and an aromatic heterocyclic group) each of which may contain about 1 to 3 hetero atoms such as O, N and S.

Examples of carbon rings in Q include $C_{3-8}$ cycloalkyl groups such as cyclopropyl, cyclobutyl, cyclopentyl and cyclohexyl; $C_{3-8}$ cycloalkenyl groups such as cyclopropenyl, 1-cyclopentenyl, 2-cyclopentenyl, 3-cyclopentenyl, 1cyclohexenyl, 2-cyclohexenyl and 3-cyclohexenyl; $C_{6-14}$ aryl groups such as phenyl, 1- or 2-naphthyl, 1-, 2- or 9anthryl, 1-, 2-, 3-, 4- or 9-phenanthryl, and 1-, 2-, 4-, 5- or 6-azulenyl.

Examples of a heterocyclic ring as Q includes 5membered cyclic groups which have 1 to 4 hetero atoms selected from the group consisting of an oxygen atom, a sulfur atom and a nitrogen atom other than a carbon atom such as 2- or 3-thienyl, 2- or 3-furyl, 2- or 3-pyrrolyl, 2-, 4- or 5-oxazolyl, 2-, 4- or 5-thiazolyl, 3-, 4- or 5pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4thiadiazolyl, 4- or 5-(1,2,3-thiadiazolyl), 1,2,5thiadiazolyl, 1,2,3-triazolyl, 1,2,4-triazolyl and 1H- or 2H-tetrazolyl; 6-membered cyclic groups which have 1 to 4 hetero atoms selected from the group consisting of an oxygen atom, a sulfur atom and a nitrogen atom other than a carbon atom such as 2-, 3- or 4-pyridyl, N-oxide-2-, 3- or 4-pyridyl, 2-, 4- or 5-pyrimidinyl, N-oxide-2-, 4- or 5pyrimidynyl, thiomorpholinyl, morpholinyl, oxoimidazinyl, dioxotriazinyl, pyrrozinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, N-oxide-3- or 4- pyridazinyl; and 5- or 8membered rings or fused rings thereof which have 1 to 4 hetero atoms selected from the group consisting of an oxygen atom, a sulfur atom and a nitrogen atom other than a carbon atom such as two-ring or three-ring fused rings which have 1 to 4 hetero atoms selected from the group consisting of an oxygen atom, a sulfur atom and a nitrogen atom other than a carbon atom such as benzofuryl, benzothiazolyl, benzoxazolyl, tetrazoro[1,5-b] pyridazinyl, triazoro[4,5-b] pyridazinyl, benzoimydazolyl, quinolyl, isoquinolyl, cinnolinyl, phthalazinyl, quinazolinyl, quinoxalinyl, indolizinyl, quinolizinyl, 1,8-naphthylizinyl, purinyl, pteridinyl, dibenzofuranyl, carbazolyl, acridinyl, phenanthlizinyl, chromanyl, benzoxazinyl, phenazinyl, phenothiazinyl and phenoxazinyl.

Of the above-mentioned groups, G is preferably a group represented by the following formula:

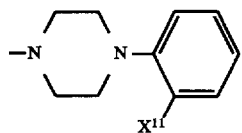

wherein $X^{11}$ represents a hydrogen atom, a $C_{1-6}$ alkyl group, a $C_{1-6}$ alkoxy group, a halogen atom or a nitro group.

Examples thereof include

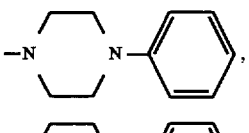

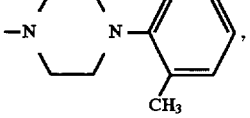

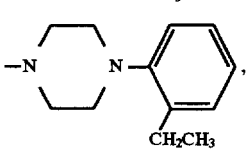

-continued

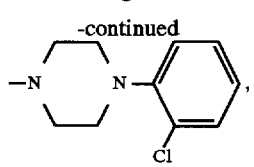

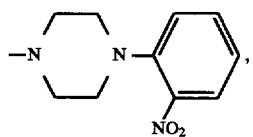

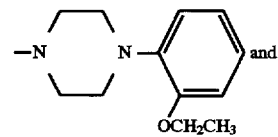

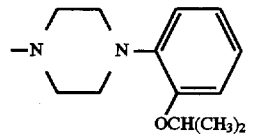

G described above may be any of the L-, D- and DL-forms. The L-form is, however, more preferred among others.

An amino acid which forms the D-acidic-α-amino acid residue represented by A in formula [I] is, for example, an amino acid with an acidic group such as carboxyl, sulfonyl or tetrazolyl at a side chain. Examples of such amino acids include D-glutamic acid, D-aspartic acid, D-cysteic acid, D-homocysteic acid, D-A-(5-tetrazolyl)alanine and D2-amino-4-(5-tetrazolyl)butyric acid. In particular, D-glutamic acid, D-aspartic acid and D-cysteic acid are preferred.

An amino acid which forms the neutral-α-amino acid residue represented by B in formula [I] is an a-amino acid. Examples of such a-amino acids include alanine, valine, norvaline, leucine, isoleucine, alloisoleucine, norleucine, tertiary leucine, y-methylleucine, phenylglycine, phenylalanine, 1-naphthylalanine, 2-naphthylalanine, proline, 4-hydroxyproline, azetidine-2-carboxylic acid, pipecolic acid (piperidine-2-carboxylic acid), 2-thienylalanine, 2-thienylglycine, 3-thienylglycine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid, 2-cyclopentylglycine and 2-cyclohexylglycine. When the above-mentioned neutral-α-amino acid exists in the L- and D-forms, the D-form is preferred. D-Leucine, D-alloisoleucine, D-tertiary leucine, D-α-methylleucine, D-phenylglycine, D-2-thienylalanine, D-2-thienylglycine, D-3-thienylglycine and D-2-cyclopentylglycine are preferred among others. α-Imino groups of these neutral-i-amino acids may be substituted by $C_{1-6}$ alkyl groups (for example, methyl, ethyl, n-propyl and t-butyl). Examples of such a-amino acids include N-methylleucine, N-methylalloisoleucine, N-methyl tertiary leucine, N-methyl γ-methylleucine and N-methylphenyl-glycine. Also for these α-amino acids, the D-form is preferred.

B described above preferably represents -NH-CHR$^2$-CO-, wherein R$^2$ represents a $C_{1-6}$ alkyl group, a $C_{3-7}$ cycloalkyl group, a $C_{3-7}$ cycloalkyl-$C_{1-3}$ alkyl group, a $C_{1-6}$ alkylthio-$C_{1-3}$ alkyl group, a $C_{3-7}$ cycloalkylthio-$C_{1-3}$ alkyl group, a $C_{1-6}$ alkoxy-$C_{1-3}$ alkyl group, a $C_{3-7}$ cycloalkoxy-$C_{1-33}$ alkyl group, a $C_{1-6}$ alkylthio group, a $C_{3-7}$ cycloalkylthio group, a $C_{1-6}$ alkoxy group or a $C_{3-7}$ cycloalkoxy group.

The $C_{1-6}$ alkyl groups represented by $R^2$ include, for example, methyl, ethyl, n-propyl, iso-propyl, n-butyl, isobutyl, (1-methyl)propyl, tert-butyl, n-pentyl, (2methyl)butyl, (3-methyl)butyl, neopentyl, n-hexyl, (2,2dimethyl)butyl and (3,3-dimethyl)butyl. In particular, $C_{4-6}$ alkyl groups such as n-butyl, iso-butyl, (1-methyl)propyl, tert-butyl, n-pentyl, (2-methyl)butyl, (3-methyl)butyl, neopentyl and n-hexyl are preferably used.

The $C_{3-7}$ cycloalkyl groups represented by $R^2$ include, for example, cyclopropyl, cyclobutyl, cyclopentyl, cyclohexyl and cycloheptyl. In particular, $C_{5-7}$ cycloalkyl groups such as cyclopentyl, cyclohexyl and cycloheptyl are preferably used.

The $C_{3-7}$ cycloalkyl-$C_{1-3}$ alkyl groups represented by $R^2$ include, for example, cyclopropylmethyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, cycloheptylmethyl and cycloheptylethyl. In particular, $C_{3-7}$ cycloalkyl-methyl groups such as cyclopropylmethyl, cyclobutylmethyl, cyclopentylmethyl, cyclohexylmethyl and cycloheptylmethyl are preferably used.

The $C_{1-6}$ alkylthio-$C_{1-3}$ alkyl groups represented by $R^2$ include, for example, methylthiomethyl, methylthioethyl, methylthiopropyl, ethylthiomethyl, ethylthioethyl, n-propylthiopropyl, iso-propylthiomethyl, n-butylthiomethyl, tert-butylthiomethyl, n-butylthioethyl, tert-butylthiopropyl and (1,1-dimethyl)propylthiomethyl. In particular, $C_{3-7}$ alkylthio-methyl groups such as iso-propylthiomethyl, n-butylthiomethyl, tert-butylthiomethyl and (1,1-dimethyl)-propylthiomethyl are preferably used.

The $C_{3-7}$ cycloalkylthio-$C_{1-3}$ alkyl groups represented by $R^2$ include, for example, cyclopropylthiomethyl, cyclopropylthioethyl, cyclopropylthiopropyl, cyclobutylthiomethyl, cyclobutylthioethyl, cyclobutylthiopropyl, cyclopentylthiomethyl, cyclopentylthioethyl, cyclohexylthiomethyl and cycloheptylthiomethyl. In particular, $C_{4-7}$ cycloalkylthio-methyl groups such as cyclobutylthiomethyl, cyclopentylthiomethyl, cyclohexylthiomethyl and cycloheptylthiomethyl are preferably used.

The $C_{1-6}$ alkoxy-$C_{1-3}$ alkyl groups represented by $R^2$ include, for example, methoxymethyl, methoxyethyl, methoxypropyl, ethoxymethyl, ethoxyethyl, n-propoxymethyl, n-propoxyethyl, iso-propoxymethyl, iso-propoxyethyl, n-butoxymethyl, n-butoxyethyl, tert-butoxymethyl, tertbutoxyethyl, n-pentyloxymethyl, n-pentyloxyethyl, (1,1dimethyl)propoxymethyl, (1,1-dimethyl)propoxyethyl, n-hexyloxymethyl and n-hexyloxyethyl. In particular, $C_{1-6}$ alkoxy-methyl groups such as methoxymethyl, ethoxymethyl, n-propoxymethyl, iso-propoxymethyl, n-butoxymethyl, tertbutoxymethyl, n-pentyloxymethyl, (1,1-dimethyl)propoxymethyl and n-hexyloxymethyl are preferably used, and isopropoxymethyl, tert-butoxymethyl, (1,1-dimethyl) propoxymethyl and n-hexyloxymethyl are more preferred among others.

The $C_{3-7}$ cycloalkoxy-$C_{1-3}$ alkyl groups represented by $R^2$ include, for example, cyclopropoxymethyl, cyclopropoxyethyl, cyclobutoxymethyl, cyclobutoxyethyl, cyclopentyloxymethyl, cyclopentyloxyethyl, cyclohexyloxymethyl and cycloheptyloxymethyl. In particular, $C_{3-7}$ cycloalkoxymethyl groups such as cyclopropoxymethyl, cyclobutoxymethyl, cyclopentyloxymethyl, cyclohexyloxymethyl and cycloheptyloxymethyl are preferably used.

The $C_{1-6}$ alkylthio groups represented by $R^2$ include, for example, methylthio, ethylthio, n-propylthio, isopropylthio, n-butylthio, tert-butylthio, n-pentylthio, (1,1-dimethyl) propylthio and n-hexylthio. In particular, $C_{3-6}$ alkylthio groups such as n-propylthio, iso-propylthio, n-butylthio, tert-butylthio, n-pentylthio, (1,1dimethyl)propylthio and n-hexylthio are preferably used.

The $C_{3-7}$ cycloalkylthio groups represented by $R^2$ include, for example, cyclopropylthio, cyclobutylthio, cyclopentylthio, cyclohexylthio and cycloheptylthio. In particular, $C_{4-7}$ cycloalkylthio groups such as cyclobutylthio, cyclopentylthio, cyclohexylthio and cycloheptylthio are preferably used.

The $C_{1-6}$ alkoxy groups represented by $R^2$ include, for example, methoxy, ethoxy, n-propoxy, iso-propoxy, n-butoxy, tert-butoxy, n-pentyloxy, (1,1-dimethyl)propoxy and n-hexyloxy. In particular, $C_{3-6}$ alkoxy groups such as n-propoxy, iso-propoxy, n-butoxy, tert-butoxy, n-pentyloxy, (1,1-dimethyl)propoxy and n-hexyloxy are preferably used.

The $C_{3-7}$ cycloalkoxy groups represented by $R^2$ include, for example, cyclopropoxy, cyclobutoxy, cyclopentyloxy, cyclohexyloxy and cycloheptyloxy. In particular, $C_{4-7}$ cyclopropoxy groups such as cyclobutoxy, cyclopentyloxy, cyclohexyloxy and cycloheptyloxy are preferably used.

As $R^2$, the $C_{1-6}$ alkyl groups are preferably used, and the $C_{4-6}$ alkyl groups (such as n-butyl, iso-butyl, (1-methyl) propyl, tert-butyl, n-pentyl, (2-methyl)butyl, (3methyl) butyl, neopentyl and n-hexyl) are more preferred among others. In particular, tert-butyl and neopentyl are most preferably used as $R_2$.

The α-amino acid residue represented by -NH-CHR$^2$-CO- described above may be any of the L-, D- and DL-forms. However, the D-form is more preferred among others.

As an amino acid which forms the L-α-amino acid residue represented by C in formula [I], used is an L-α-amino acid usually known in the art. Examples of such L-α-amino acids include glycine, L-alanine, L-valine, L-norvaline, L-leucine, L-isoleucine, L-tertiary leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine and L-proline. In particular, L-leucine, L-norleucine and L-tryptophan are preferred. α-amino groups of these L-a-amino acids may be substituted by $C_{1-6}$ alkyl groups (for example, methyl, ethyl, n-propyl and t-butyl). Examples of such L-a-amino acids include L-Nmethylleucine, L-N-methylnorleucine and L-N(α)-methyltryptophan.

As an amino acid which forms the D-α-amino acid residue with the aromatic ring group represented by E in formula [I], used is a D-α-amino acid having an aromatic ring group at a side chain. Preferred examples thereof include D-tryptophan, D-5-methyltryptophan, D-phenylalanine, D-tyrosine, D-1-naphthylalanine, D-2-naphthylalanine, D-3-benzothienylalanine, D-4-biphenylalanine and D-pentamethylphenylalanine. D-Tryptophan and D-5methyltryptophan are preferred, and particularly, D-tryptophan is more preferred. The α-amino groups of the D-α-amino acids having the aromatic rings may be substituted by $C_{1-6}$ alkyl groups (for example, methyl, ethyl, n-propyl and t-butyl). Further, the amino group of the indole ring of D-tryptophan may be substituted by a hydrocarbon group such as a $C_{1-6}$ alkyl group (for example, methyl, ethyl, n-propyl or t-butyl), a $C_{3-8}$ cycloalkyl group (for example, cyclopentyl or cyclohexyl), a $C_{6-12}$ aryl group (for example, phenyl, or 4-methylphenyl) or $C_{7-15}$ aralkyl (for example, benzyl or phenethyl), or an acyl group such as a $C_{1-6}$ aliphatic acyl group (preferably $C_{1-6}$ alkanoyl) (for example, formyl, acetyl or propionyl), a $C_{4-9}$ alicyclic acyl group (preferably $C_{5-7}$ cycloalkyl carbonyl) (for example, cyclopentanecarbonyl or cyclohexanecarbonyl), a $C_{7-15}$ arylacyl group (preferably $C_{6-12}$ aryl carbonyl) (for example, benzoyl or 4-methylbenzoyl), a $C_{8-16}$ aralkylacyl group (preferably $C_{6-12}$ aryl-$C_{2-4}$ alkanoyl) (for example, phenylacetyl, 2-phenylpropionyl, 3-phenylpropionyl or diphenylacetyl) or a $C_{1-6}$ alkoxycarbonyl group (for example, methoxycarbonyl or ethoxycarbonyl). Examples of such α-amino acids include D-N(α)-methyltryptophan, D-N-methylphenylalanine, D-N-methyltyrosine, D-$N^{in}$-methyltryptophan, D-$N^{in}$-ethyl-tryptophan, D-$N^{in}$-formyltryptophan and D-$N^{in}$-acetyl-tryptophan. D-$N^{in}$-methyltryptophan, D-$N^{in}$-formyltryptophan and D-$N^{in}$-acetyltryptophan are more preferred.

E is preferably D-Trp-($N^{in}$-$R^3$)- wherein $R^3$ is a hydrogen atom, a $C_{1-6}$ alkyl group, a $C_{3-7}$ cycloalkyl group, —$COR^4$ ($R^4$ is a hydrogen atom, a $C_{1-6}$ alkyl group, a $C_{6-15}$ aryl group or a $C_{6-15}$ aryl-$C_{1-3}$ alkyl group), -$COOR^5$ ($R^5$ is a hydrogen atom, a $C_{1-6}$ alkyl group, a $C_{6-15}$ aryl group or a $C_{6-15}$ aryl-$C_{1-13}$ alkyl group), or -$CONHR^6$ ($R^6$ is a hydrogen atom, a $C_{1-6}$ alkyl group, a $C_{6-15}$ aryl group or a $C_{6-15}$ aryl-$C_{1-3}$ alkyl group). $R^3$ binds to the N atom of an indole group in the triptophan residue.

The $C_{1-6}$ alkyl groups represented by $R^3$ include, for example, methyl, ethyl, n-propyl, iso-propyl, n-butyl, isobutyl, (1-methyl)propyl, tert-butyl, n-pentyl, (2-methyl)butyl, (3-methyl)butyl, neopentyl, n-hexyl, (2,2-dimethyl)butyl and (3,3-dimethyl)butyl. In particular, $C_{1-3}$ alkyl groups such as methyl, ethyl, n-propyl and iso-propyl are preferably used.

The $C_{3-7}$ cycloalkyl groups represented by $R^3$ include, for example, cyclopropyl, cyclobutyl, cyclopentyl, cyclohexyl and cycloheptyl. In particular, $C_{5-7}$ cycloalkyl groups such as cyclopentyl, cyclohexyl and cycloheptyl are preferably used.

The $C_{1-6}$ alkyl groups represented by $R^4$, $R^5$ and $R^6$ include, for example, methyl, ethyl, n-propyl, iso-propyl, n-butyl, iso-butyl, (1-methyl)propyl, tert-butyl, n-pentyl, (2-methyl)butyl, (3-methyl)butyl, neopentyl, n-hexyl, (2,2dimethyl)butyl and (3,3-dimethyl)butyl. In particular, $C_{1-3}$ alkyl groups such as methyl, ethyl, n-propyl and iso-propyl are preferably used.

The $C_{615}$ aryl groups represented by $R^4$, $R^5$ and $R^6$ include, for example, phenyl, α-naphthyl and β-naphthyl, and phenyl is particularly preferred.

The $C_{6-15}$ aryl-$C_{1-3}$ alkyl groups represented by $R^4$, $R^5$ and $R^6$ include, for example, benzyl, phenethyl, phenylpropyl, α-naphthylmethyl, α-naphthylethyl, α-naphthylpropyl, β-naphthylmethyl, β-naphthylethyl and β-naphthylpropyl. In particular, $C_{6-15}$ aryl-methyl groups such as benzyl, α-naphthylmethyl and β-naphthylmethyl are preferably used.

Specifically, —$COR^4$ is, for example, formyl, acetyl, propionyl, butyryl, isobutyryl, isovaleryl, pivaloyl, n-pentylcarbonyl, benzoyl or phenylacetyl. -$COOR^5$ is, for example, methoxycarbonyl, ethoxycarbonyl, phenoxycarbonyl and benzyloxycarbonyl. —$CONHR^6$ is, for example, carbamoyl, methylaminocarbonyl, ethylaminocarbonyl, n-propylaminocarbonyl, iso-propylaminocarbonyl, n-butylaminocarbonyl, iso-butylaminocarbonyl, phenylaminocarbonyl or benzylaminocarbonyl.

It is particularly preferred that $R^3$ is a hydrogen atom or —$COR^4$ (wherein $R^4$ represents a hydrogen atom, a $C_{1-6}$ alkyl group, a $C_{6-15}$ aryl group or a $C_{6-15}$ aryl-$C_{1-3}$ alkyl group). Specifically, a hydrogen atom, formyl and acetyl are preferred.

In the hexapeptide represented by formula [I], the preferable embodiments of each parameter are as follows:

X has L-configuration.

Y has L-configuration.

A is selected from the group consisting of D-glutamic acid, D-aspartic acid, D-cysteic acid and D-β-(5-tetrazolyl)alanine residue.

B has D-configuration.

B is selected from the group consisting of 1-aminocyclopropane-1-carboxylic acid, 1-aminocyclobutane-1-carboxylic acid, 1-aminocyclopentane-1-carboxylic acid, 1aminocyclohexane-1-carboxylic acid and 1-aminocycloheptane1-carboxylic acid residue.

B is selected from the group consisting of D-leucine, D-alloisoleucine, D-tertiaryleucine, D-gammamethylleucine, D-phenylglycine, D-2-thienylglycine, D-3-thienylglycine, D-cyclopentylglycine, D-phenylalanine, D-2-thienylalanine, D-valine, D-2-furylglycine and D-3-furylglycine residue.

C is selected from the group consisting of L-leucine, L-isoleucine, L-valine, L-norleucine and L-a-amino acid residue having aromatic moiety.

E is D-tryptophan, or a derivative thereof, D-1naphthylalanine, D-2-naphthylalanine, D-benzothienylalanine, D-4-bisphenylalanine and D-pentamethylphenylalanine residue.

The derivative of tryptophan is selected from the group consisting of D-$N^{in}$-methyltryptophan, D-$N^{in}$formyltryptophan and D-$N^{in}$-acetyltryptophan residue.

Preferable combinations of each parameter include such as those in which A is D-aspartic acid residue; X is tryptophan, L-(β-phenylpiperazine amide)aspartic acid, L-(β-4(2-methoxyphenyl)piperazine amide) aspartic acid, L-($N^8$-phenylacetyl)ornithine, L-($N^4$-[indol-3-yl]acetyl) ornithine, L-(4-benzyloxy)proline, L-(N5benzyl)glutamine or L-($N^8$-[indol-3-yl]ethyl)asparagine residue; Y is L-leucine, L-aspartic acid or L-O-benzylserine residue; B is D-leucine, D-γ-methylleucine, D2-thienylglycine or D-3-thienylglycine residue; C is selected from the group consisting of L-leucine, L-phenylalanine and L-tryptophan residue; and E is D-tryptophan residue.

The esters of the compound [I] include alkyl esters of those which have a carboxyl group as a side chain of an α-amino acid residue. The alkyl groups are $C_{1-6}$ alkyl groups such as methyl, ethyl, n-propyl, iso-propyl, n-butyl, isobutyl, tert-butyl, n-pentyl and n-hexyl.

Typical cyclic hexapeptides [I] of the present invention are shown as follows. In the following list, liquid secondary ion mass spectrography is abbreviated as LSIMS.

Among them, cyclo(-D-Asp-Asp(R1)-Asp-D-Thg(2)-Leu-D-Trp-) wherein Asp is aspartic acid, Asp(R1) is an aspartic acid β4-phenylpiperidineamide residue, Thg(2) is a 2-(2-thienyl)glycine residue, Leu is a leucine residue and Trp is a tryptophan residue, is preferable.

1 cyclo[-D-Asp-Ala-Asp-D-Leu-Leu-D-Trp-]
2 cyclo[-D-Asp-Ala-D-Asp-D-Leu-Leu-D-Trp-]
3 cyclo[-D-Asp-Ala-Glu-D-Leu-Leu-D-Trp-]
4 cyclo[-D-Asp-Ala-D-Glu-D-Leu-Leu-D-Trp-]
5 cyclo[-D-Asp-Gly-Ala-D-Leu-Leu-D-Trp-]
6 cyclo[-D-Asp-Asp-Ala-D-Leu-Leu-D-Trp-]
7 cyclo[-D-Asp-Glu-Ala-D-Leu-Leu-D-Trp-]
8 cyclo[-D-Asp-Trp-Asp-D-Leu-Leu-D-Trp-]
9 cyclo[-D-Asp-Pro-Asp-D-Leu-Leu-D-Trp-]
10 cyclo[-D-Asp-Asn($CH_2$Ph)-Asp-D-Leu-Leu-D-Trp-]
11 cyclo[-D-Asp-Asn($CH_2CH_2$Ph)-Asp-D-Leu-Leu-D-Trp-)

12 cyclo[-D-Asp-Asn(CH₂CH₂-Ind)-Asp-D-Leu-Leu-D-Trp-]
13 cyclo[-D-Asp-Hyp(Bzl)-Asp-D-Leu-Leu-D-Trp-]
14 cyclo[-D-Asp-Hyp-Asp-D-Leu-Leu-D-Trp-]
15 cyclo[-D-Asp-D-Ala-Asp-D-Leu-Leu-D-Trp-] LSIMS (M+H+)=714 (theoretical value)=714
16 cyclo[-D-Asp-Asp-Asp-D-Leu-Leu-D-Trp-] LSIMS(M+H+)=758 (theoretical value)=758
17 cyclo[-D-Asp-Val-Asp-D-Leu-Leu-D-Trp-] LSIMS(M+H+)=742 (theoretical value)=742
18 cyclo[-D-Asp-Leu-Asp-D-Leu-Leu-D-Trp-] LSIMS(M+H+)=756 (theoretical value)=756
19 cyclo[-D-Asp-Phe-Asp-D-Leu-Leu-D-Trp-] LSIMS(M+H+)=790 (theoretical value)=790
20 cyclo[-D-Asp-Ser(Bzl)-Asp-D-Leu-Leu-D-Trp-] LSIMS (M+H+)=820 (theoretical value)=820
21 cyclo[-D-Asp-Thr(Bzl)-Asp-D-Leu-Leu-D-Trp-] LSIMS (M+H+)=834 (theoretical value)=834
22 -D-Asp-Trp(For)-Asp-D-Leu-Leu-D-Trp-] LSIMS(M+H+)=857 (theoretical value)=857
23 cyclo[-D-Asp-Nal(1)-Asp-D-Leu-Leu-D-Trp-] LSIMS (M+H+)=840 (theoretical value)=840
24 cyclo[-D-Asp-D-Pro-Asp-D-Leu-Leu-D-Trp-] LSIMS (M+H+)=740 (theoretical value)=740
25 cyclo[-D-Asp-Azc-Asp-D-Leu-Leu-D-Trp-] LSIMS(M+H+)=725 (theoretical value)=725
26 cyclo[-D-Asp-Pip-Asp-D-Leu-Leu-D-Trp-] LSIMS(M+H+)=753 (theoretical value)=753
27 cyclo[-D-Asp-D-Asp-Ala-D-Leu-Leu-D-Trp-] LSIMS (M+H+)=714 (theoretical value)=714
28 cyclo[-D-Asp-D-Glu-Ala-D-Leu-Leu-D-Trp-] LSIMS (M+H+)=728 (theoretical value)=728
29 cyclo[-D-Asp-Asp-D-Ala-D-Leu-Leu-D-Trp-] LSIMS (M+H+)=714 (theoretical value)=714
30 cyclo[-D-Asp-Asp-Pro-D-Leu-Leu-D-Trp-] LSIMS(M+H+)=740 (theoretical value)=740
31 cyclo[-D-Asp-Asp-D-Pro-D-Leu-Leu-D-Trp-] LSIMS (M+H+)=740 (theoretical value)=740
32 cyclo[-D-Asp-Asp-Leu-D-Leu-Leu-D-Trp-] LSIMS(M+H+)=756 (theoretical value)=756
33 cyclo[-D-Asp-Asp-Trp-D-Leu-Leu-D-Trp-] LSIMS(M+H+)=829 (theoretical value)=829
34 cyclo[-D-Asp-Trp-Glu-D-Leu-Leu-D-Trp-] LSIMS(M+H+)=844 (theoretical value)=844
35 cyclo[-D-Asp-Trp-Leu-D-Leu-Leu-D-Trp-] LSIMS(M+H+)=828 (theoretical value)=828
36 cyclo[-D-Asp-Trp-Pro-D-Leu-Leu-D-Trp-] LSIMS(M+H+)=811 (theoretical value)=811
37 cyclo[-D-Asp-Trp-Ser-D-Leu-Leu-D-Trp-] LSIMS(M+H+)=801 (theoretical value)=801
38 cyclo[-D-Asp-Trp-Ser(Bzl)-D-Leu-Leu-D-Trp-] LSIMS (M+H+)=892 (theoretical value)=892
39 cyclo[-D-Asp-Ala-Asp-D-tLeu-Leu-D-Trp-] LSIMS(M+H+)=714 (theoretical value)=714
40 cyclo[-D-Glu-Ala-Gly-D-Leu-Leu-D-Trp-] LSIMS(M+H+)=670 (theoretical value)=670
41 cyclo[-D-Glu-Ala-Asp-D-Leu-Leu-D-Trp-] LSIMS(M+H+)=728 (theoretical value)=728
42 cyclo[-D-Asp-Trp-Asp-D-Leu-Leu-D-Trp(For)-] LSIMS (M+H+)=857 (theoretical value)=857
43 cyclo[-D-Asp-Trp-Asp-D-Leu-Leu-D-Trp(Ac)-] LSIMS (M+H+)=871 (theoretical value)=871
44 cyclo[-D-Asp-Trp-Asp-D-Acpe-Leu-D-Trp-] LSIMS(M+H+)=827 (theoretical value)=827
45 cyclo[-D-Asp-Trp-Asp-D-Phg-Leu-D-Trp-] LSIMS(M+H+)=849 (theoretical value)=849
46 cyclo[-D-Asp-Sar-Asp-D-Leu-Leu-D-Trp-] LSIMS(M+H+)=714 (theoretical value)=714
47 cyclo[-D-Asp-N-MeLeu-Asp-D-Leu-Leu-D-Trp-] LSIMS(M+H+)=770 (theoretical value)=770
48 cyclo[-D-Asp-N-MePhe-Asp-D-Leu-Leu-D-Trp-] LSIMS(M+H+)=804 (theoretical value)=804
49 cyclo[-D-Asp-Trp-Asp-D-Thg(3)-Leu-D-Trp-] LSIMS (M+H+)=855 (theoretical value)=855
50 cyclo[-D-Asp-Trp-Asp-D-Thi-Leu-D-Trp-] LSIMS(M+H+)=869 (theoretical value)=869
51 cyclo[-D-Asp-Trp-Asp-D-aIle-Leu-D-Trp-] LSIMS(M+H+)=829 (theoretical value)=829
52 cyclo[-D-Asp-Trp-Asp-D-Val-Leu-D-Trp-] LSIMS(M+H+)=815 (theoretical value)=815
57 cyclo[-D-Asp-Ala-Asp-D-Leu-Phe-D-Trp-] LSIMS(M+H+)=748 (theoretical value)=748
58 cyclo[-D-Asp-Ala-Asp-D-Leu-Trp-D-Trp-] LSIMS(M+H+)=787 (theoretical value)=787
59 cyclo[-D-Glu-Gly-Ala-D-Leu-Leu-D-Trp-] LSIMS(M+H+)=670 (theoretical value)=670
60 cyclo[-D-Asp-Trp-Asp-D-Phe-Leu-D-Trp-] LSIMS(M+H+)=863 (theoretical value)=863
61 cyclo[-D-Asp-Trp-Asp-Achx-Leu-D-Trp-] LSIMS(M+H+)=841 (theoretical value)=841
62 cyclo[-D-Asp-Gln(CH₂Ph)-Asp-D-Leu-Leu-D-Trp-] LSIMS(M+H+)=861 (theoretical value)=861
63 cyclo[-D-Asp-Gln(CH₂CH₂Ph)-Asp-D-Leu-Leu-D-Trp-] LSIMS(M+H+)=875 (theoretical value)=875
64 cyclo[-D-Asp-Gln(CH₂CH₂-Ind)-Asp-D-Leu-Leu-D-Trp-] LSIMS(M+H+)=914 (theoretical value)=914
65 cyclo[-D-Asp-Arg(Tos)-Asp-D-Leu-Leu-D-Trp-] LSIMS(M+H+)=953 (theoretical value)=953
66 cyclo[-D-Asp-Lys(Mtr)-Asp-D-Leu-Leu-D-Trp-] LSIMS(M+H+)=983 (theoretical value)=983
67 cyclo[-D-Asp-N-MeTrp-Asp-D-Leu-Leu-D-Trp-] LSIMS(M+H+)=843 (theoretical value)=843
68 cyclo[-D-Asp-Asn(MeNCH₂CH₂Ph)-Asp-D-Leu-Leu-D-Trp-] LSIMS(M+H+)=875 (theoretical value)=875
69 cyclo[-D-Asp-Asn(CH₂CHMePh)-Asp-D-Leu-Leu-D-Trp-] LSIMS(M+H+)=875 (theoretical value)=875
70 cyclo[-D-Asp-Asp(R1)-Asp-D-Leu-Leu-D-Trp-] LSIMS (M+H+)=902 (theoretical value)=902
71 cyclo[-D-Asp-Asp(R2)-Asp-D-Leu-Leu-D-Trp-] LSIMS (M+H+)=901 (theoretical value)=901
72 cyclo[-D-Asp-Asp(R3)-Asp-D-Leu-Leu-D-Trp-] LSIMS (M+H+)=859 (theoretical value)=859
73 cyclo[-D-Asp-Asp(R4)-Asp-D-Leu-Leu-D-Trp-] LSIMS (M+H+)=873 (theoretical value)=873
74 cyclo[-D-Asp-Asp(R5)-Asp-D-Leu-Leu-D-Trp-] LSIMS (M+H+)=887 (theoretical value)=887
75 cyclo[-D-Asp-Asp(R6)-Asp-D-Leu-Leu-D-Trp-] LSIMS (M+H+)=868 (theoretical value)=868
76 cyclo[-D-Asp-Glu(R3)-Asp-D-Leu-Leu-D-Trp-] LSIMS (M+H+)=873 (theoretical value)=873
77 cyclo[-D-Asp-Glu(R4)-Asp-D-Leu-Leu-D-Trp-] LSIMS (M+H+)=887 (theoretical value)=887
78 cyclo[-D-Asp-Glu(R5)-Asp-D-Leu-Leu-D-Trp-] LSIMS (M+H+)=901 (theoretical value)=901
83 cyclo[-D-Asp-His-Asp-D-Leu-Leu-D-Trp-] LSIMS(M+H+)=780 (theoretical value)=780
84 cyclo[-D-Asp-His(Bom)-Asp-D-Leu-Leu-D-Trp-] LSIMS(M+H+)=900 (theoretical value)=900
85 cyclo[-D-Asp-His(Bzl)-Asp-D-Leu-Leu-D-Trp-] LSIMS (M+H+)=870 (theoretical value)=870
86 cyclo[-D-Asp-D,L-Tic-Asp-D-Leu-Leu-D-Trp-] LSIMS (M+H+)=802 (theoretical value)=802
87 cyclo[-D-Asp-Tpr-Asp-D-Leu-Leu-D-Trp-] LSIMS(M+H+)=758 (theoretical value)=758
91 cyclo[-D-Asp-Asp(Trp-NHEt)-Asp-D-Leu-Leu-D-Trp-] LSIMS(M+H+)=971 (theoretical value)=971

92 cyclo[-D-Asp-Asp(Trp-NHBzl)-Asp-D-Leu-Leu-D-Trp-] LSIMS(M+H+)=1033 (theoretical value)=1033
93 cyclo[-D-Asp-Asp(D-Trp-NHBzl)-Asp-D-Leu-Leu-D-Trp-] LSIMS(M+H+)=1033 (theoretical value)=1033
94 cyclo[-D-Asp-Asp(Trp-NHCH₂CH₂Ph)-Asp-D-Leu-Leu-D-Trp-] LSIMS(M+H+)=1047 (theoretical value)=1047
95 cyclo[-D-Asp-Trp-Asp-D-Leu-Leu-D-Trp(Me)-] LSIMS (M+H+)=843 (theoretical value)=843
96 cyclo[-D-Asp-Asp(R1-Asp-D-Thg(2)-Leu-D-Trp-] LSIMS(M+H+)=928 (theoretical value)=928
97 cyclo[-D-Asp-Asn(CH₂CH₂-Ind)-Asp-D-Phg-Leu-D-Trp-]
98 cyclo[-D-Asp-Asn(CH₂CH₂-Ind)-Asp-D-Thg(3)-LeuD-Trp-]
99 cyclo[-D-Asp-Asn(CH₂CH₂-Ind)-Asp-Acbu-Leu-D-Trp-]
100 cyclo[-D-Asp-Asn(CH₂CH₂-Ind)-Asp-Acpe-Leu-D-Trp-]
101 cyclo[-D-Asp-Asn (CH₂CH₂-Ind) -Asp-Achx-Leu-D-Trp-]
102 cyclo[-D-Asp-Asn(CH₂CH₂-Ind)-Asp-Achp-Leu-D-Trp-]
103 cyclo[-D-Asp-Asn(CH₂CH₂-Ind)-Asp-D-Thg(2)-LeuD-Trp(Me)-]
104 cyclo[-D-Asp-Asn(CH₂CH₂-Ind)-Asp-D-Thg(2)-LeuD-Trp(For)-]
105 cyclo[-D-Cta-Trp-Asp-D-Val-Leu-
106 cyclo[-D-Cta-Trp-Asp-D-Leu-Leu-D-Trp-]
107 cyclo[-D-Cta-Trp-Asp-D-Thg(2)-Leu-D-Trp-]
108 cyclo[-D-Cta-Trp-Asp-D-Thg(3)-Leu-D-Trp-]
109 cyclo[-D-Cta-Asn(CH₂CH₂-Ind)-Asp-D-Val-Leu-D-Trp-]
110 cyclo[-D-Cta-Asn(CH₂CH₂-Ind)-Asp-D-Leu-Leu-D-Trp-]
111 cyclo[-D-Cta-Asn(CH₂CH₂-Ind)-Asp-D-Thg(2)-Leu-D-Trp-]
112 cyclo[-D-Cta-Asn(CH₂CH₂-Ind)-Asp-D-Thg(3)-Leu-D-Trp-]
113 cyclo[-D-Cta-Asn(CH₂CH₂-Ind)-Asp-D-Thg(2)-LeuD-Trp(Me)-]
114 cyclo[-D-Cta-Asn(CH₂CH₂-Ind)-Asp-D-Thg(2)-LeuD-Trp(For)-]
115 cyclo[-D-Asp-Gln(CH₂Ph)-Asp-D-Thg(3)-Leu-D-Trp-]
116 cyclo[-D-Asp-Gln (CH₂Ph)-Asp-D-Phg-Leu-D-Trp- ]
117 cyclo[-D-Asp-Gln (CH₂Ph)-Asp-D-Leu-Leu-D-Trp-]
118 cyclo[-D-Asp-Gln(CH₂Ph)-Asp-D-Val-Leu-D-Trp-]
119 cyclo[-D-Asp-Gln(CH₂Ph)-Asp-D-aIle-Leu-D-Trp-]
120 cyclo[-D-Asp-Gln (CH₂Ph)-Asp-D-tLeu-Leu-D-Trp-]
121 cyclo[-D-Asp-Gln(CH₂Ph)-Asp-D-Thg(2)-Leu-D-Trp(Me)-]
122 cyclo[-D-Asp-Gln(CH₂Ph)-Asp-D-Thg(3)-Leu-D-Trp(Me)-]
123 cyclo[-D-Asp-Gln(CH₂Ph)-Asp-D-Thg(2)-LeuD-Trp(For)-]
124 cyclo[-D-Asp-Gln(CH₂Ph)-Asp-D-Thg(3)-LeuD-Trp(For)-]
125 cyclo[-D-Asp-Gln(CH₂CH₂Ph)-Asp-D-Thg(2)-Leu-D-Trp-]
126 cyclo[-D-Asp-Gln(CH₂CH₂Ph)-Asp-D-Thg(3)-Leu-D-Trp-]
127 cyclo[-D-Asp-Gln(CH₂CH₂-Ind)-Asp-D-Thg(2)-LeuD-Trp-]
128 cyclo[-D-Asp-Gln(CH₂CH₂-Ind)-Asp-D-Thg(3)-LeuD-Trp-]
129 cyclo[-D-Cta-Gln(CH₂Ph)-Asp-D-Thg(2)-Leu-D-Trp-]
130 cyclo[-D-Cta-Gln(CH₂Ph)-Asp-D-Thg(3)-Leu-D-Trp-]
131 cyclo[-D-Cta-Gln(CH₂CH₂Ph)-Asp-D-Thg(2)-Leu-D-Trp-]
132 cyclo[-D-Cta-Gln(CH₂CH₂Ph)-Asp-D-Thg(3)-Leu-D-Trp-]
133 cyclo[-D-Cta-Gln(CH₂CH₂-Ind)-Asp-D-Thg(2)-LeuD-Trp-]
134 cyclo[-D-Cta-Gln(CH₂CH₂-Ind)-Asp-D-Thg(3)-LeuD-Trp-)]
135 cyclo[-D-Asp-Asn(CH₂CH₂-Ind)-Asp-D-Val-Leu-D-Trp-]
136 cyclo[-D-Asp-Asp(R7)-Asp-D-Thg(2)-Leu-D-Trp-]
137 cyclo[-D-Asp-Asp(R8)-Asp-D-Thg(2)-Leu-D-Trp-]
138 cyclo[-D-Asp-Asp(R9)-Asp-D-Thg(2)-Leu-D-Trp-]
139 cyclo[-D-Asp-Asp(R10)-Asp-D-Thg(2)-Leu-D-Trp-]
140 cyclo[-D-Asp-Asp(R11)-Asp-D-Thg(2)-Leu-D-Trp-]
141 cyclo[-D-Asp-Asp(R12)-Asp-D-Thg(2)-Leu-D-Trp-]
142 cyclo[-D-Asp-Asp(R13)-Asp-D-Thg(2)-Leu-D-Trp-]
143 cyclo[-D-Asp-Asp(R14)-Asp-D-Thg(2)-Leu-D-Trp-]
144 cyclo[-D-Asp-Asp(R15)-Asp-D-Thg(2)-Leu-D-Trp-]
145 cyclo[-D-Asp-Asp(R16)-Asp-D-Thg(2)-Leu-D-Trp-]
146 cyclo[-D-Cta-Asp(R11)-Asp-D-Thg(2)-Leu-D-Trp-]
147 cyclo[-D-Cta-Asp(R7)-Asp-D-Thg(2)-Leu-D-Trp-]
148 cyclo[-D-Cta-Asp(R8)-Asp-D-Thg(2)-Leu-D-Trp-]
149 cyclo[-D-Cta-Asp(R9)-Asp-D-Thg(2)-Leu-D-Trp-]
150 cyclo[-D-Cta-Asp(R10)-Asp-D-Thg(2)-Leu-D-Trp-]
151 cyclo[-D-Cta-Asp(R11)-Asp-D-Thg(2)-Leu-D-Trp-]
152 cyclo[-D-Cta-Asp(R12)-Asp-D-Thg(2)-Leu-D-Trp-]
153 cyclo[-D-Cta-Asp(R13)-Asp-D-Thg(2)-Leu-D-Trp-]
154 cyclo[-D-Cta-Asp(R14)-Asp-D-Thg(2)-Leu-D-Trp-]
155 cyclo[-D-Cta-Asp(R15)-Asp-D-Thg(2)-Leu-D-Trp-]
156 cyclo[-D-Cta-Asp(R16)-Asp-D-Thg(2)-Leu-D-Trp-]
157 cyclo[-D-Asp-Asp(R1)-Asp-D-Cpg-Leu-D-Trp-]
158 cyclo[-D-Asp-Asp(R7)-Asp-D-Cpg-Leu-D-Trp-]
159 cyclo[-D-Asp-Asp(R8)-Asp-D-Cpg-Leu-D-Trp-]
160 cyclo[-D-Asp-Asp(R9)-Asp-D-Cpg-Leu-D-Trp-]
161 cyclo[-D-Asp-Asp(R10)-Asp-D-Cpg-Leu-D-Trp-]
162 cyclo[-D-Asp-Asp(R11)-Asp-D-Cpg-Leu-D-Trp-]
163 cyclo[-D-Asp-Asp(R12)-Asp-D-Cpg-Leu-D-Trp-]
164 cyclo[-D-Asp-Asp(R13)-Asp-D-Cpg-Leu-D-Trp-]
165 cyclo[-D-Asp-Asp(R14)-Asp-D-Cpg-Leu-D-Trp-]
166 cyclo[-D-Asp-Asp(R15)-Asp-D-Cpg-Leu-D-Trp-]
167 cyclo[-D-Asp-Asp(R16)-Asp-D-Cpg-Leu-D-Trp-]
168 cyclo[-D-Cta-Asp(R1)-Asp-D-Cpg-Leu-D-Trp-]
169 cyclo[-D-Cta-Asp(R7)-Asp-D-Cpg-Leu-D-Trp-]
170 cyclo[-D-Cta-Asp(R8)-Asp-D-Cpg-Leu-D-Trp-]
171 cyclo[-D-Cta-Asp(R9)-Asp-D-Cpg-Leu-D-Trp-]
172 cyclo[-D-Cta-Asp(R10)-Asp-D-Cpg-Leu-D-Trp-]
173 cyclo[-D-Cta-Asp(R11)-Asp-D-Cpg-Leu-D-Trp-]
174 cyclo[-D-Cta-Asp(R12)-Asp-D-Cpg-Leu-D-Trp-]
175 cyclo[-D-Cta-Asp(R13)-Asp-D-Cpg-Leu-D-Trp-]
176 cyclo[-D-Cta-Asp(R14)-Asp-D-Cpg-Leu-D-Trp-]
177 cyclo[-D-Cta-Asp(R15)-Asp-D-Cpg-Leu-D-Trp-]
178 cyclo[-D-Cta-Asp(R16)-Asp-D-Cpg-Leu-D-Trp-]
179 cyclo[-D-Asp-Asp(R7)-Asp-D-Leu-Leu-D-Trp-]
180 cyclo[-D-Asp-Asp(R8)-Asp-D-Leu-Leu-D-Trp-]
181 cyclo[-D-Asp-Asp(R9)-Asp-D-Leu-Leu-D-Trp-]
182 cyclo[-D-Asp-Asp(R10)-Asp-D-Leu-Leu-D-Trp-]
183 cyclo[-D-Asp-Asp(R11)-Asp-D-Leu-Leu-D-Trp-]
184 cyclo[-D-Asp-Asp(R12)-Asp-D-Leu-Leu-D-Trp-]
185 cyclo[-D-Asp-Asp(R13)-Asp-D-Leu-Leu-D-Trp-]
186 cyclo[-D-Asp-Asp(R14)-Asp-D-Leu-Leu-D-Trp-]
187 cyclo[-D-Asp-Asp(R15)-Asp-D-Leu-Leu-D-Trp-]
188 cyclo[-D-Asp-Asp(R16)-Asp-D-Leu-Leu-D-Trp-]
189 cyclo[-D-Cta-Asp(R1)-Asp-D-Leu-Leu-D-Trp-]
190 cyclo[-D-Cta-Asp(R7)-Asp-D-Leu-Leu-D-Trp-]
191 cyclo[-D-Cta-Asp(R8)-Asp-D-Leu-Leu-D-Trp-]
192 cyclo[-D-Cta-Asp(R9)-Asp-D-Leu-Leu-D-Trp-]

193 cyclo[-D-Cta-Asp(R10)-Asp-D-Leu-Leu-D-Trp-]
194 cyclo[-D-Cta-Asp(R11)-Asp-D-Leu-Leu-D-Trp-]
195 cyclo[-D-Cta-Asp(R12)-Asp-D-Leu-Leu-D-Trp-]
196 cyclo[-D-Cta-Asp(R13)-Asp-D-Leu-Leu-D-Trp-]
197 cyclo[-D-Cta-Asp(R14)-Asp-D-Leu-Leu-D-Trp-]
198 cyclo[-D-Cta-Asp(R15)-Asp-D-Leu-Leu-D-Trp-]
199 cyclo[-D-Cta-Asp(R16)-Asp-D-Leu-Leu-D-Trp-]
200 cyclo[-D-Asp-Asp(R1)-Asp-D-Thi-Leu-D-Trp-]
201 cyclo[-D-Asp-Asp(R1)-Asp-D-Phe-Leu-D-Trp-]
202 cyclo[-D-Cta-Asp(R1)-Asp-D-Thi-Leu-D-Trp-]
203 cyclo[-D-Cta-Asp(R1)-Asp-D-Phe-Leu-D-Trp-]

In the above formula, R1 to R16 represent the following formula:

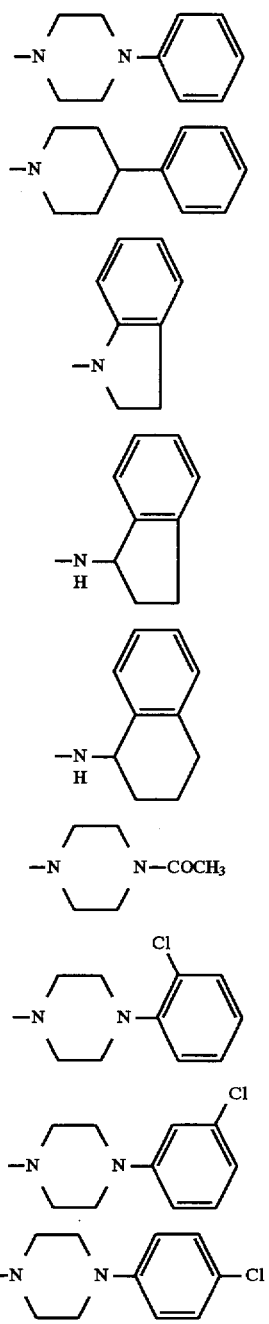

-continued

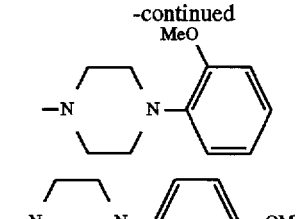

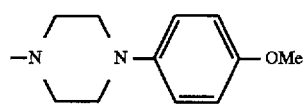

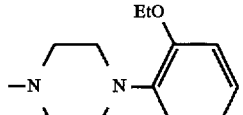

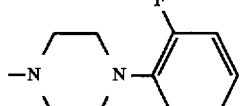

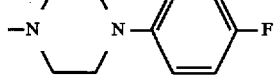

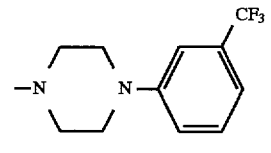

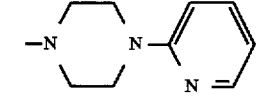

The cyclic hexapeptides [I] of the present invention can be produced by methods for peptide synthesis known in the art, which may be either solid phase synthesis methods or liquid phase synthesis methods. In some cases, the liquid phase synthesis methods are preferred. Examples of such methods for peptide synthesis include methods described in M. Bodansky and M. A. Ondetti, *Peptide Synthesis*, Interscience, New York (1966); F. M. Finn and K. Hofmann, *The Proteins*, Vol. 2, edited by H. Nenrath and R. L. Hill, Academic Press, New York, (1976); N. Izumiya et al., *Peptide Gosei no Kiso to Jikken (Fundamentals and Experiments of Peptide Synthesis)*, Maruzen (1985); H. Yazima, S. Sakakibara et al., *Seikagaku Jikken Koza (Course of Biochemical Experiments)*, 1, edited by Biochemical Society of Japan, Tokyo Kagaku Dojin (1977); H. Kimura et al., *Zoku Seikagaku Jikken Koza (Course of Biochemical Experiments, second series)*, 2, edited by Biochemical Society of Japan, Tokyo Kagaku Dojin (1987); and J. M. Stewart and J. D. Young, *Solid Phase Peptide Synthesis*, Pierce Chemical Company, Illinois (1984), which describe azide methods, chloride methods, acid anhydride methods, mixed acid anhydride methods, DCC methods, active ester methods, methods using Woodward reagent K, carbodiimidazole methods, oxidation-reduction methods, DCC/HONB methods and methods using BOP reagents.

The cyclic hexapeptides [I] of the present invention can be produced by condensing a first starting material having a reactive carboxyl group corresponding to one of two kinds of fragments which are separated at any position of its peptide bond with a second starting material having a reactive amino group corresponding to the other fragment, subsequently eliminating protective groups of the C-terminal α-carboxyl group and the N-terminal α-amino group of the resulting compound concurrently or stepwise, thereafter conducting intramolecular condensation of both by methods known in the art to obtain a cyclic compound, and then, eliminating protective groups by methods known in the art, if the resulting condensed product has any protective groups.

The above starting materials are usually amino acid and/or peptide fragments which, taken together, form the cyclic hexapeptide of the desired formula [I] or a salt thereof. They are usually linear or branched. The reactive carboxyl group means a carboxyl group itself or an activated carboxyl group. The reactive amino group means an amino group itself or an activated amino group. One of the two functional groups taking part in the condensation reaction is usually activated.

The carboxyl group and the amino group which do not take part in the condensation reaction are usually protected before the condensation reaction.

Protection of functional groups should not affect the reaction of the starting materials. The protective groups, elimination of the protective groups, and activation of functional groups related to the reaction can be suitably selected from groups or methods known in the art.

Examples of the protective groups for the amino groups of the starting materials include benzyloxycarbonyl, t-butyloxycarbonyl, t-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl. The protective groups for the carboxyl groups include, for example, alkyl esters (such as esters of methyl, ethyl, propyl, butyl, t-butyl, cyclopentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, benzyloxycarbonylhydrazide, t-butyloxycarbonylhydrazide and tritylhydrazide.

The hydroxyl group of serine can be protected, for example, by esterification or etherification. Examples of groups suitable for this esterification include lower aliphatic acyl groups such as acetyl, arylacyl groups such as benzoyl, and carbonic acid-derived groups such as benzyloxycarbonyl and ethoxycarbonyl. Examples of groups suitable for the etherification include benzyl, tetrahydropyranyl and t-butyl. However, the hydroxyl group of serine is not always required to be protected.

Examples of the protective groups for the phenolic hydroxyl group of tyrosine include benzyl, 2,6-dichlorobenzyl, 2-nitrobenzyl, 2-bromobenzyloxycarbonyl and t-butyl. However, the phenolic hydroxyl group of tyrosine is not always required to be protected.

Methionine may be protected in the form of sulfoxides.

The protective groups for the imidazole ring of histidine include p-toluenesulfonyl, 4-methoxy-2,3,6-trimethylbenzenesulfonyl, 2,4-dinitrophenyl, benzyloxymethyl, t-butoxymethyl, t-butoxycarbonyl, trityl and 9-fluorenylmethyloxycarbonyl. However, the imidazole ring is not always required to be protected.

The protective groups for the indole ring of tryptophan include formyl, 2,4,6-trimethylbenzensulfonyl, 2,4,6-trimethoxybenzenesulfonyl, 4-methoxy-2,3,6-trimethylbenzenesulfonyl, 2,2,2-trichloroethoxycarbonyl and diphenylphosphinothioyl. However, the indole ring is not always required to be protected.

Examples of the activated carboxyl groups of the starting materials include the corresponding acid anhydrides, azides and active esters (esters of alcohols such as pentachlorophenol, 2,4,5-trichlorophenol, 2,4-dinitrophenol, cyanomethyl alcohol, p-nitrophenol, N-hydroxy-5-norbornene-2,3-dicarboxyimide, N-hydroxysuccinimide, N-hydroxyphthalimide and N-hydroxybenzotriazole. Examples of the activated amino acid groups of the raw materials include the corresponding phosphoric acid amides.

The condensation reaction can be conducted in the presence of a solvent(s). The solvent(s) can be appropriately selected from the solvents commonly used in peptide condensation reactions. Examples of the solvents include anhydrous or hydrous dimethylformamide, dimethyl sulfoxide, pyridine, chloroform, dioxane, dichloromethane, tetrahydrofuran, acetonitrile, ethyl acetate, N-methylpyrrolidone and appropriate mixtures thereof.

The reaction temperature is appropriately selected from the temperature range commonly used in peptide bond-forming reactions, usually from the range of about -20° to about 30° C.

Intramolecular cyclization reaction can be conducted at any position of the peptide by methods known in the art. For example, the protective group of the C-terminal α-carboxyl group of the protected peptide is first eliminated by methods known in the art, and then, the carboxyl group is activated by methods known in the art, followed by elimination of the protective group of the N-terminal α-amino group by methods known in the art and intramolecular cyclization. The protective groups of the C-terminal α-carboxyl group and the N-terminal α-amino group of the protected peptide may be concurrently eliminated, followed by intramolecular cyclization according to known condensation reaction. In some cases, intramolecular cyclization reaction is preferably conducted in a highly diluted state.

Examples of methods for eliminating the protective groups include catalytic reduction in the presence of a catalyst such as palladium black or Pd-carbon in a stream of hydrogen, acid treatment with anhydrous hydrogen fluoride, methanesulfonic acid, trifluoromethanesulfonic acid, trifluoroacetic acid or mixtures thereof, and reduction with sodium in liquid ammonia. The elimination reaction by the above-mentioned acid treatment is generally conducted at a temperature between -20° and 40° C. In the acid treatment, it is effective to add a cation trapping agent such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is eliminated by thiophenol treatment. The formyl group used as the protective group for the indole ring of tryptophan may be eliminated by either (i) alkali treatment using dilute sodium hydroxide, dilute ammonia or the like, or (ii) the above-mentioned elimination by the acid treatment in the presence of 1,2-ethanedithiol, 1,4-butanedithiol or the like.

After completion of the reaction, the cyclic hexapeptide [I] thus obtained is collected by conventional separation and purification methods of peptides such as extraction, distribution, reprecipitation, recrystallization, column chromatography and high performance liquid chromatography.

The cyclic hexapeptides [I] of the present invention can be obtained by methods known in the art as the metal salts, the salts of bases or basic compounds, the inorganic acid addition salts, the organic acid salts and the like, and particularly as pharmaceutically acceptable acid addition salts such as the salts of inorganic acids (for example, hydrochloric acid, sulfuric acid and phosphoric acid) or organic acids (for example, acetic acid, propionic acid, citric acid, tartaric acid, malic acid, oxalic acid and methanesulfonic acid).

In this specification, amino acids and peptides are indicated by the abbreviations commonly used in the art or adopted by the IUPAC-IUB Commission on Biochemical Nomenclature. For example, the following abbreviations are used:

| | |
|---|---|
| Gly | Glycine |
| Sar | Sarcosine (N-methylglycine) |
| Ala | Alanine |
| Val | Valine |
| Nva | Norvaline |
| Ile | Isoleucine |
| aIle | Alloisoleucine |
| Nle | Norleucine |
| Leu | Leucine |
| N-MeLeu | N-Methylleucine |
| tLeu | t-Leucine |
| γMeLeu | γ-Methylleucine |
| Met | Methionine |
| Arg | Arginine |
| Arg(Tos) | $N^g$-p-Toluenesulfonylarginine |
| Lys | Lysine |
| Lys(Mtr) | N(ε)-(4-Methoxy-2,3,6-trimethyl-benzenesulfonyl)lysine |
| Orn | Ornithine |
| Orn(COPh) | N(δ)-Benzoylornithine |
| Orn(COCH$_2$Ph) | N(δ)-Phenylacetylornithine |
| Orn(COCH$_2$CH$_2$Ph) | N(δ)-(3-Phenylpropionyl)ornithine |
| Orn(COCH$_2$-Ind) | N(δ)-({Indole-3-yl}acetyl)ornithine |
| His | Histidine |
| His(Bom) | N(π)-Benzyloxymethylhistidine |
| His(Bzl) | N(τ)-Benzylhistidine |
| Asp | Aspartic acid |
| Asn(CH$_2$Ph) | $N^4$-Benzylasparagine |
| Asn(CH$_2$CH$_2$Ph) | $N^4$-Phenethylasparagine |
| Asn(CH$_2$CH$_2$-Ind) | $N^4$-(2-{Indole-3-yl}ethyl)asparagine |
| Asn(Me.CH$_2$CH$_2$Ph) | $N^4$-Methyl-$N^4$-phenethylasparagine |
| Asn(CH$_2$CHMePh) | $N^4$-({2-phenyl}propyl)asparagine |
| Asp(R1) | Aspartic acid β-4-phenylpiperazineamide |
| Asp(R2) | Aspartic acid β-4-phenylpiperidineamide |
| Asp(R3) | Aspartic acid β-indolineamide |
| Asp(R4) | Aspartic acid β-1-aminoindanamide |
| Asp(R5) | Aspartic acid β-1-aminotetrahydronaphthaleneamide |
| Asp(R6) | Aspartic acid β-4-acetylpiperazineamide |
| Asp(R7) | Aspartic acid β-4-(2-chlorophenyl)piperazineamide |
| Asp(R8) | Aspartic acid β-4-(3-chlorophenyl)piperazineamide |
| Asp(R9) | Aspartic acid β-4-(4-chlorophenyl)piperazineamide |
| Asp(R10) | Aspartic acid β-4-(2-methoxyphenyl)piperazineamide |
| Asp(R11) | Aspartic acid β-4-(4-methoxyphenyl)piperazineamide |
| Asp(R12) | Aspartic acid β-4-(2-ethoxyphenyl)piperazineamide |
| Asp(R13) | Aspartic acid β-4-(2-fluorophenyl)piperazineamide |
| Asp(R14) | Aspartic acid β-4-(4-fluorophenyl)piperazineamide |
| Asp(R15) | Aspartic acid β-4-(3-trifluoromethylphenyl) piperazineamide |
| Asp(R16) | Aspartic acid β-4-(2-pyridyl)piperazineamide |
| Glu | Glutamic acid |
| Gln(CH$_2$Ph) | $N^5$-Benzylglutamine |
| Gln(CH$_2$CH$_2$Ph) | $N^5$-Phenethylglutamine |
| Gln(CH$_2$CH$_2$-Ind) | $N^5$-(2-{Indole-3-yl}ethyl)glutamine |
| Glu(R3) | Glutamic acid γ-indolineamide |
| Glu(R4) | Glutamic acid γ-1-aminoindanamide |
| Glu(R5) | Glutamic acid γ-1-aminotetrahydronaphthaleneamide |

-continued

| | |
|---|---|
| Cys | Cysteine |
| Cta | Cysteic acid |
| Ser | Serine |
| Ser(Bzl) | O-Benzylserine |
| Thr | Threonine |
| Thr(Bzl) | O-Benzylthreonine |
| Pro | Proline |
| Tpr | Thioproline |
| Hys | 4-Hydroxyproline |
| Hys(Bzl) | 4-Benzyloxyproline |
| Azc | Azetidine-2-carboxylic acid |
| Pip | Pipecolic acid (piperidine-2-carboxylic acid) |
| Phe | Phenylalanine |
| N-MePhe | N-Methylphenylalanine |
| Tyr | Tyrosine |
| Trp | Tryptophan |
| mTrp | 5-Methyltryptophan |
| N-MeTrp | N(α)-Methyltryptophan |
| Trp(Me) | $N^{in}$-Methyltryptophan |
| Trp(For) | $N^{in}$-Formyltryptophan |
| Trp(Ac) | $N^{in}$-Acethyltryptophan |
| Phg | Phenylglycine |
| Nal(1) | 1-Naphthylalanine |
| Nal(2) | 2-Naphthylalanine |
| Thi | 2-Thienylalanine |
| Thg(2) | 2-Thienylglycine |
| Thg(3) | 3-Thienylglycine |
| Acpr | 1-Aminocyclopropane-1-carboxylic acid |
| Acbu | 1-Aminocyclobutane-1-carboxylic acid |
| Acpe | 1-Aminocyclopentane-1-carboxylic acid |
| Achx | 1-Aminocyclohexane-1-carboxylic acid |
| Achp | 1-Aminocycloheptane-1-carboxylic acid |
| Tic | Tetrahydroisoquinoline-2-carboxylic acid |

Protective groups and reagents commonly used in this specification are indicated by the following abbreviations:

| | |
|---|---|
| AcOEt | Ethyl acetate |
| Boc | t-Butoxycarbonyl |
| Bzl | Benzyl |
| BrZ | 2-Bromobenzyloxycarbonyl |
| ClZ | 2-Chlorobenzyloxycarbonyl |
| Tos | p-Toluenesulfonyl |
| For | Formyl |
| OBzl | Benzyl ester |
| OPac | Phenacyl ester |
| ONB | HONB ester |
| TFA | Trifluoroacetic acid |
| TEA | Triethylamine |
| IBCF | Isobutyl chloroformate |
| DMF | N,N-Dimethylformamide |
| DCC | N,N'-Dicyclohexylcarbodiimide |
| DCU | N,N'-Dicyclohexylurea |
| HONB | N-Hydroxy-5-norbornene-2,3-dicarboxyimide |
| HOBt | 1-Hydroxybenzotriazole |
| DCM | Dichloromethane |
| THF | Tetrahydrofuran |

The compositions of the present invention comprising pharmacological carriers containing an effective amount of cyclic hexapeptides having antagonistic activity on endothelin receptors can be used as prophylactic and/or therapeutic compositions for the treatment of pulmonary circulatory diseases. In the present invention, the pulmonary circulatory diseases include, for example, primary pulmonary hypertension, pulmonary fibrosis, pulmonary embolism, pulmonary congestion and cataplectic pulmonary arteriectasis. However, it is to be understood that this list is not intended to limit the scope of the present invention.

An increase in pulmonary arterial pressure due to an increase in pulmonary vascular resistance is widely observed in patients suffering from pulmonary circulatory diseases. The increase in pulmonary vascular resistance includes a primary increase such as primary pulmonary hypertension and a secondary increase caused by pulmonary embolism. Either case finally causes pulmonary insufficiency. The increase in pulmonary vascular resistance is considered to induce a decrease in the survival time of patients suffering from pulmonary circulatory diseases, which necessitates the treatment for stimulating a reduction in pulmonary arterial vascular resistance. Using an induction experiment model of monocrotaline, a kind of plant alkaloid, as a model of pulmonary hypertension, the effect of the compounds of the present invention having antagonistic activity on endothelin receptors was studied. As a result, it was found that the compounds significantly decrease the pulmonary arterial pressure and have activity for inhibiting right ventricular hypertrophy.

Accordingly, compositions comprising pharmaceutically acceptable carriers containing an effective amount of the cyclic hexapeptides having antagonistic activity on endothelin receptors can be used as prophylactic and/or therapeutic drugs for the treatment of pulmonary circulatory diseases. The cyclic hexapeptides having antagonistic activity on endothelin receptors used in the present invention are safe, low-toxic compounds.

When the cyclic hexapeptides having antagonistic activity on endothelin receptors are used as the prophylactic and/or therapeutic drugs for the treatment of pulmonary circulatory diseases, the compounds can be given orally or parenterally (for example, intravenously, subcutaneously, intramuscularly, intraperitoneally, intrarectally or sublingually) to warm-blooded animals (such as rabbits, dogs, cats, rats, mice, monkeys, cattle and humans). The form of preparations may be either oral preparations (such as powders, tablets, granules and capsules) or parenteral preparations (such as injections, suppositories and sustained release preparations). They may be used in combination with other drugs (such as vasodilator drugs, cardiac stimulants, drugs for inhibiting thrombocytopenia and anticoagulants), or may be used as mixtures therewith. These preparations can be prepared by methods known in the art. The amount of compound [I] contained in pharmaceutical compositions of the present invention is about 0.01% to about 20% (w/w).

When the compounds are given parenterally, they are usually given in the solution form, for example, in the injection form. Although the dose varies depending upon the object to which the preparations are given, the organ to which they are given, the symptom, the route of administration, and etc, it is advantageous that they are intravenously injected in the injection form in a dose of about 0.01 to about 100 mg/kg of body weight per operation time, preferably about 0.01 to about 50 mg/kg, and more preferably about 0.05 to about 20 mg/kg. When the compounds are given orally, they are given before surgery in a dose of about 5 mg to about 1 g/kg of body weight, and preferably about 10 to 100 mg/kg. The injections include hypodermic injections, intradermic injections, intramuscular injections and drip infusions, as well as intravenous injections. Such injections are prepared by methods known in the art, namely, by dissolving, suspending or emulsifying the compounds having antagonistic activity on endothelin receptors in aseptic aqueous or oily solutions. Aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic surface active agents (for example, Polysorbate 80 and HCO50). Oily solutions include sesame oil and soybean oil, and may be used in combination with solubilizing adjuvants such as benzyl benzoate and benzyl alcohol. The preparations may further contain buffers (for example, phosphate buffer and sodium acetate buffer), soothing agents (for example, benzalkonium chloride and procaine hydrochloride), stabilizing agents (for example, human serum albumin and polyethylene glycol), preservatives (for example, benzyl alcohol and phenol), etc. The injections thus prepared are usually filled into appropriate ampuls. When the oral preparations such as powders, tablets, granules and capsules are prepared, pharmaceutically acceptable carriers may be incorporated therein. The carriers include excipients (for example, lactose and starch), lubricants (for example, magnesium stearate and talc), binders (for example, hydroxypropyl cellulose, hydroxypropylmethyl cellulose and macrogold) and disintegrators (starch and carboxymethyl cellulose calcium). Additives such as antiseptics (for example, benzyl alcohol, chlorobutanol, methyl p-hydroxybenzoate and propyl p-hydroxybenzoate), antioxidants, colorants and sweeteners can be further used as required.

The pharmaceutically acceptable salts of the cyclic hexapeptides having antagonistic activity on endothelin receptors of the present invention include alkali metal salts (for example, sodium salts and potassium salts), alkaline earth metal salts (for example, calcium salts and magnesium salts), ammonium salts, organic base salts (for example, pyridine salts and triethylamine salts), inorganic acid salts (for example, hydrochlorides, sulfates and nitrates) and organic acid salts (for example, acetates, oxalates and p-toluene-sulfonates).

When the cyclic hexapeptides are used as the prophylactic and/or therapeutic drugs, they must be carefully purified to avoid the presence of bacteria and pyrogenic substances.

The present invention will be described in more detail with the following Reference Examples, Examples and Experimental Example. It is understood of course that they are not intended to limit the scope of the present invention. When the D- and L-forms exist for the α-amino acids used in Examples and Experimental Example, the L-forms are used unless otherwise specified.

Reference Example 1

Five grams of the disodium salt of a cyclic peptide represented by formula cyclo(-D-Asp-Asp(R1)-Asp-D-Thg (2)-Leu-D-Trp-) (wherein Asp represents an aspartic acid residue, Asp(R1) represents aspartic acid β-4-phenylpiperidineamide, Thg(2) represents a 2-(2-thienyl) glycine residue, Leu represents a leucine residue, and Trp represents a tryptophan residue) described in Japanese Unexamined Patent Publication No. 6-9689 (hereinafter referred to as peptide A) and 11.4 g of zinc acetate (dihydrate) were each dissolved in 250 ml portions of distilled water, and both the resulting solutions were mixed with each other. After standing at 4° C. for one day, the mixed solution was centrifuged at 3,000 rpm in a 05PR-22 centrifuge (Hitachi, Ltd., Japan), and the supernatant was discarded. The resulting precipitate was dispersed in distilled water again, followed by further centrifugation to wash out free chemicals. A small amount of distilled water was added to the collected precipitate to disperse it again. Then, the resulting dispersion was lyophilized to obtain 4.45 g of crude zinc salt of peptide A as a dried powder.

The resulting dried powder was extracted with a 50 mM solution of ethylenediaminetetraacetatic acid (EDTA) by shaking for 3 hours, and determined by high performance liquid chromatography (HPLC). As a result, the amount of peptide A contained in the dried powder was 83% (w/w).

Reference Example 2

The disodium salt of peptide A was dissolved in physiological saline to prepare an injection.

Example 1

To 1.65 g of a lactic acid-glycolic acid copolymer (lactic acid/glycolic acid: 75/25 (mol%), weight average molecular weight: 15,038, number average molecular weight: 5,195, Wako Pure Chemical Industries, Ltd., Japan), 3.3 g (2.5 ml) of dichloromethane was added to dissolve the copolymer.

350 mg of the crude zinc salt of peptide A obtained in Reference Example 1 was dispersed in 2.5 ml of dichloromethane.

Both the solution and the dispersion were mixed with each other, and the mixture was stirred with a homogenizer (Polytron) for about 30 seconds, followed by standing at 4° C. for one hour. Five ml of dichloromethane was further added thereto, and the mixture was stirred with the Polytron homogenizer again. Then, the mixture was poured into 800 ml of a 0.1% (w/w) aqueous solution of polyvinyl alcohol (EG-40, Nippon Synthetic Chemical Industry Co, Ltd., Japan) previously adjusted to 18° C., and mixed by use of a turbine type homomixer at 6,000 rpm to prepare an O/W emulsion. The O/W emulsion was stirred at room temperature for 3 hours to evaporate dichloromethane, thereby solidifying an oily phase. Centrifugation was conducted at about 2,000 rpm in 05PR-22 centrifuge (Hitachi, Ltd., Japan), and the supernatant was discarded. The resulting precipitate was dispersed in distilled water again, followed by further centrifugation. Then, 50 mg of D-mannitol was added to the collected biodegradable matrix, and a small amount of distilled water was further added thereto to disperse it again. The resulting dispersion was lyophilized to obtain a powder.

The resulting microcapsules were extracted with a 50 mM solution of EDTA containing 30% acetonitrile by shaking for 3 hours, and determined by HPLC. As a result, the microcapsules contained 15.8 mg of crude peptide zinc salt per 100 mg of microcapsules in terms of the 2Na salt of peptide A.

Example 2

The microcapsules obtained in Example 1 were dispersed in a disperse medium (in which carboxymethyl cellulose, polysorbate 80 and mannitol were dissolved in distilled water in amounts of 5 mg, 1 mg and 50 mg per ml of distilled water, respectively) to prepare an injection.

Experimental Example 1

In order to evaluate the compound having antagonistic activity on endothelin receptors as a prophylactic and/or therapeutic drug for the treatment of pulmonary circulatory diseases, a study was conducted using an induction experiment model of monocrotaline, a kind of plant alkaloid.

Seven-week-old Wister rats (male) weighing 250 to 300 g were anesthetized with pentobarbital (50 mg/kg, intraperitoneal administration), followed by subcutaneous administration of monocrotaline (100 mg/kg). Then, osmotic pressure type mini pumps into which a vehicle (physiological saline) or 45 mg of the 2Na salt of peptide A dissolved in physiological saline was included were subcutaneously mounted at the backs thereof. The osmotic pressure type mini pumps were each changed by new pumps after two weeks. Four weeks after administration of monocrotaline, each of the rats was anesthetized with pentobarbital, and the chest thereof was opened under artificial respiration. A catheter was inserted into the right ventricle to measure the right ventricular pressure which is an index of the pulmonary arterial pressure. Then, the heart thereof was extracted, and the weight of the right ventricle and that of the left ventricle and the septum were measured to determine the weight ratio of the right ventricle to the heart. For untreated rats of the same week age, similar measurement was carried out, and this group of rats was taken as a normal group. The comparison of a vehicle group with a group treated with the 2Na salt of peptide A was carried out by use of the t-test, and a significance level of 5% or less was considered to be a significant difference. Results are shown in Table 1.

TABLE 1

| | Number of Rats | Right Ventricular Systolic Pressure (mm Hg) | Weight of Right Ventricle/Weight of Heart (%) |
|---|---|---|---|
| Normal Group | 9 | 29 ± 1 | 19.1 ± 0.8 |
| Vehicle Group | 9 | 64 ± 6 | 34.6 ± 0.9 |
| Group Treated with 2Na Salt of Peptide A | 7 | 47 ± 2* | 30.8 ± 1.4* |

The value of each parameter in Table 1: mean value +standard error, *: p<0.05

In the monocrotaline-treated group, an increase in right ventricular systolic pressure, namely an increase in pulmonary arterial pressure, was observed, compared with the normal group. Further, the ratio of the right ventricle to the whole heart increased. These results show the characteristics observed in pulmonary hypertension. Compared with the vehicle group, the group treated with the 2Na salt of peptide A showed a significant decrease in pulmonary arterial pressure, and the ratio of the right ventricle to the whole heart was also significantly lowered. From the results described above, it has been revealed that the cyclic hexapeptides having antagonistic activity on endothelin receptors of the present invention inhibit an increase in pulmonary arterial pressure considered to be caused by an increase in pulmonary vascular resistance, and also inhibit right ventricular hypertrophy. These results show that the cyclic hexapeptides having antagonistic activity on endothelin receptors of the present invention are useful as the prophylactic and/or therapeutic compositions for treatment of pulmonary circulatory diseases such as pulmonary hypertension.

What is claimed is:

1. A method for the prophylaxis or treatment of pulmonary hypertension in a mammal in need thereof which comprises administering to such mammal an effective amount of a compound of the formula [I]:

 [I]

wherein X and Y each is an α-amino acid residue having D-, L-form or DL-form, A is a D-acidic-α-amino acid residue, B is a neutral-α-amino acid residue having D- or L-form, C is an L-α-amino acid residue and E is a D-α-amino acid residue which as an aromatic at a side chain group; or a pharmaceutically acceptable ester or salt thereof with a pharmaceutically acceptable excipient, carrier or diluent.

2. A method according to claim 1, wherein X and Y are L-α-amino acid residues.

3. A method according to claim 1, wherein X is

wherein G is

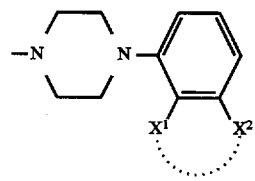

wherein $X^1$ and $X^2$ each is a hydrogen atom, a $C_{1-6}$ alkyl group, a $C_{1-6}$ alkoxy group, a halogen atom or a nitro group, or $X^1$ and $X^2$ combine together to form a ring.

4. A method according to claim 3, wherein $X^2$ is a hydrogen atom.

5. A method according to claim 3, wherein G is

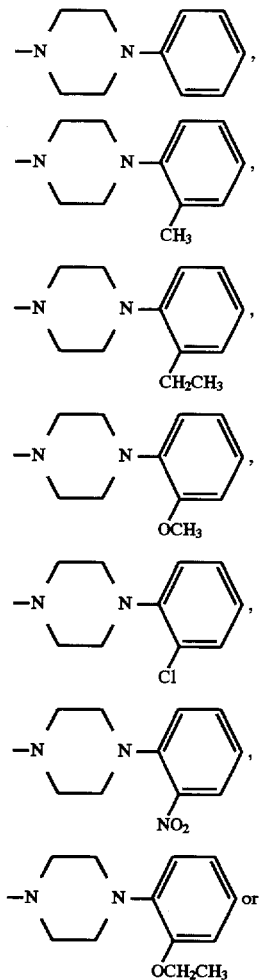

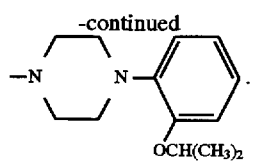

6. A method according to claim 1, wherein A is a D-α-amino acid residue which has a carboxyl, a sulfonyl or a tetrazolyl group.

7. A method according to claim 6, wherein A is a D-glutamic acid, a D-aspartic acid, a D-cysteic acid, a D-homocysteic acid, a D-β-(5-tetrazolyl)alanine or a D-2-amino-4(5tetrazolyl)butyric acid residue.

8. A method according to claim 1, wherein B is a D-neutral α-amino acid residue.

9. A method according to claim 1, wherein B is —NH—$CHR^2$—CO— wherein $R^2$ is a $C_{1-6}$ alkyl group, a $C_{3-7}$ cycloalkyl group, a $C_{3-7}$ cycloalkyl-$C_{1-3}$ alkyl group, a $C_{1-6}$ alkylthio-$C_{1-3}$ alkyl group, a $C_{3-7}$ cycloalkylthio-$C_{1-3}$ alkyl group, a $C_{1-6}$ alkoxy-$C_{1-3}$ alkyl group, a $C_{3-7}$ cycloalkoxy-$C_{1-3}$ alkyl group, a $C_{1-6}$ alkylthio group, a $C_{3-7}$ cycloalkylthio group, a $C_{1-6}$ alkoxy group or a $C_{3-7}$ cycloalkoxy group.

10. A method according to claim 1, wherein C is an L-leucine, an L-norleucine or an L-tryptophan residue, each of which α-amino group may be substituted with a $C_{1-6}$- alkyl group.

11. A method according to claim 1, wherein E is a D-tryptophan, a D-phenylalanine, a D-tyrosine, a D-2-naphthylalanine, a D-3-benzothienylalanine, a D-4-bisphenylalanine or a D-pentamethylphenylalanine residue.

12. A method according to claim 1, wherein E is -D-Trp ($N^{in}$—$R^3$)— in which $R^3$ is bound to the N-atom of the indole group of the tryptophan residue and $R^3$ is (1) a hydrogen atom, (2) a $C_{1-6}$ alkyl group, (3) a $C_{3-7}$ cycloalkyl group, (4) —$COR^4$ wherein $R^4$ is a hydrogen atom, a $C_{1-6}$ alkyl group, a $C_{6-15}$ aryl group or a $C_{6-15}$ aryl-$C_{1-3}$ alkyl group, (5) —$COOR^5$ wherein $R^5$ is a $C_{1-6}$ alkyl group, a $C_{6-15}$ aryl group or a $C_{6-15}$ aryl-$C_{1-3}$ alkyl group, or (6) —$CONHR^6$ wherein $R^6$ is a hydrogen atom, a $C_{1-6}$ alkyl group, a $C_{6-15}$ aryl group or a $C_{6-15}$ aryl-$C_{1-3}$ alkyl group.

13. A method according to claim 1, wherein X is Ala, Gly, Asp, Glu, Trp, Pro, $N^4$-benzylasparagine, $N^4$-phenethylasparagine, $N^4$-[2-(indole-3-yl)ethyl] asparagine, 4benzyloxyproline, 4-hydroxyproline, Val, Leu, Phe, O-benzylserine, O-benzylthreonine, $N^{in}$-formyltryptophan, 3-(1-naphtyl)alanine, azetidine-2-carboxylic acid, pipecolic acid, sarcosine, N-methylleucine, N-methylphenylalanine, $N^5$-benzylglutamine, $N^5$-phenetylglutamine, $N^5$-[2-indole-3-yl)ethyl]glutamine, $N^9$-p-toluenensulfonylarginine, N(ε)-(4-methoxy-2,3,6-trimethyl-benzenesulfonyl)lysine, N(α)-methyltryptophan, $N^4$-phenetylasparagine, $N^4$-[(2-phenyl)propryl]asparagine, Asp(R1), Asp(R2), Asp(R3), Asp(R4), Asp(R5), Asp(R6), Asp(R7), Asp(R8), Asp(R9), Asp(R10), Asp(R11), Asp (R12), Asp(R13), Asp(R14), Asp(R15), Asp(R16), glutamic acid γ-indolineamide, glutamic acid γ-1-aminoindanamide, glutamic acid γ1-aminotetrahydronaphthaleneamide, His, N(π)-benzyloxymethylhistidine, N(π)-benzylhistidine, tetrahydroisoquinoline-2-carboxylic acid, thioproline, Asp(Trp-NHEt), Asp(Trp-NHBzl), Asp(Trp-NHCH$_2$CH$_2$Ph) or Asn(CH$_2$CH$_2$-Ind), wherein R1 is
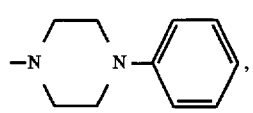
R2 is
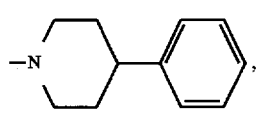
R3 is
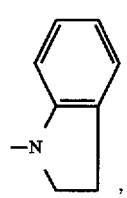
R4 is
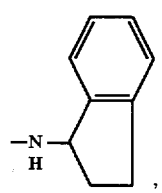
R5 is
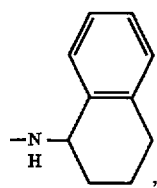
R6 is
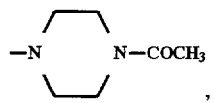
R7 is
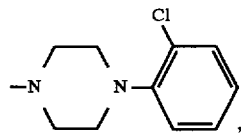
R8 is
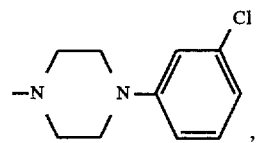
R9 is
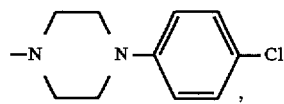
R10 is
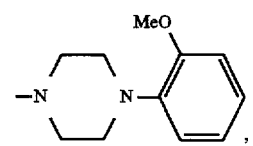
R11 is
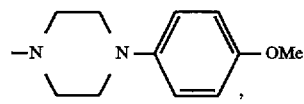
R12 is
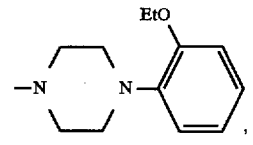
R13 is
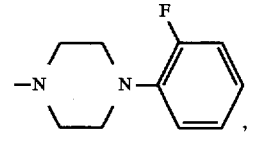
R14 is
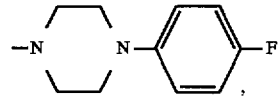
R15 is
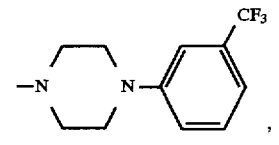
and R16 is

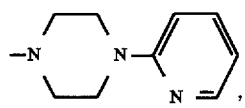

respectively;

Y is Asp, Glu, Ala, Pro, Leu, Trp or O-benzylserine; A is D-Asp, D-Glu or D-Cysteic acid; B is Leu, 1-aminocyclopentane-1-carboxylic acid, phenylglycine, 2-(3-thienyl)glycine, 3-(2-thienyl)alanine, Ile, Val, Phe, 1-aminocyclohexane-1-carboxylic acid, 2-(2-thienyl)glycine, 1-aminocyclobutane-1-carboxylic acid, 1-aminocycloheptane-1-carboxylic acid or cyclopentylglycine; C is Leu, Phe or Trp, and E is Trp, $N^{in}$-formyltryptophan, $N^{in}$-acetyltryptophan or $N^{in}$-methyltryptophan.

14. A method according to claim 1, wherein the cyclic hexapeptide is a peptide of the formula [II]:

cyclo(-D-Asp-Asp(R1)-Asp-D-Thg(2)-Leu-D-Trp)  [II]

wherein Asp(R1) is an aspartic acid β-4-phenylpiperidineamide residue, and Thg(2) is a 2-(2-thienyl) glycine residue.

15. A method for prophylaxis or treatment of primary pulmonary hypertension in a mammal in need thereof which comprises administering to such mammal an effective amount of the disodium salt of a compound of the formula [II]:

cyclo(-D-Asp-Asp(R1)-Asp-D-Thg(2)-Leu-D-Trp-)  [II]

wherein Asp(R1) is an aspartic acid β-4-phenylpiperidineamide residue, and Thg(2) is a 2-(2-thienyl) glycine residue with a pharmaceutically acceptable excipient, carrier or diluent.

* * * * *

UNITED STATES PATENT AND TRADEMARK OFFICE
CERTIFICATE OF CORRECTION

PATENT : 5,753,619
DATED : May 19, 1998
INVENTOR(S) : Watanabe et al

It is certified that error appears in the above-identified patent and that said Letters Patent is hereby corrected as shown below:

Column 26, line 63, change "as" to --has--.

Column 28, line 15, change "5 tetrazolyl" to --5-tetrazolyl--.

Column 28, line 50, change "4benzyloxyproline" to --4-benzyloxyproline--.

Column 28, line 63, change "γ1" to --γ-1--.

Signed and Sealed this

Eleventh Day of May, 1999

*Attest:*

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,753,619
DATED : May 19, 1998
INVENTOR(S) : Watanabe et al

It is certified that error appears in the above-identified patent and that said Letters Patent is hereby corrected as shown below:

Column 26, line 63, change "which as an aromatic at a side chain group" to --which has an aromatic at a side chain--.

Column 28, line 15, change "5 tetrazolyl" to -- 5-tetrazolyl--.

Column 28, line 50, change "4benzyloxyproline" to --4-benzyloxyproline--.

Column 28, line 63, change " γ1" to --γ-1--.

This certificate supersedes Certificate of Correction issued January 12, 1999 and May 11, 1999.

Signed and Sealed this

Tenth Day of August, 1999

Q. TODD DICKINSON

*Attest:*

*Attesting Officer*   Acting Commissioner of Patents and Trademarks

UNITED STATES PATENT AND TRADEMARK OFFICE
CERTIFICATE OF CORRECTION

PATENT NO. : 5,753,619
DATED : May 19, 1998
INVENTOR(S) : Watanabe et al

It is certified that error appears in the above-identified patent and that said Letters Patent is hereby corrected as shown below:

Column 26, line 63, change "which as an aromatic at a side chain" to --which has an aromatic ring group at a side chain--

Column 28, line 15, change "5 tetrazolyl" to -- 5-tetrazolyl--.

Column 28, line 50, change "4benzyloxyproline" to --4-benzyloxyproline--.

Column 28, line 63, change " γ1" to --γ-1--.

This certificate supersedes Certificates of Correction issued January 12, 1999 and May 11, 1999.

Signed and Sealed this

Eleventh Day of April, 2000

Attest:

Q. TODD DICKINSON

Attesting Officer

Director of Patents and Trademarks